(12) United States Patent
Rand et al.

(10) Patent No.: US 11,278,447 B2
(45) Date of Patent: Mar. 22, 2022

(54) PORTABLE THERMAL THERAPY AND SUPPORT APPARATUS FOR EMERGENCY MEDICAL TREATMENT

(71) Applicants: David Rand, Boca Raton, FL (US); William Rand, Boca Raton, FL (US); Felipe Echeverri, Pinecrest, FL (US)

(72) Inventors: David Rand, Boca Raton, FL (US); William Rand, Boca Raton, FL (US); Felipe Echeverri, Pinecrest, FL (US)

(73) Assignee: David Rand, Boca Raton, FL (US)

( * ) Notice: Subject to any disclaimer, the term of this patent is extended or adjusted under 35 U.S.C. 154(b) by 213 days.

(21) Appl. No.: 16/582,723

(22) Filed: Sep. 25, 2019

(65) Prior Publication Data

US 2021/0085519 A1    Mar. 25, 2021

(51) Int. Cl.
*A61F 7/02* (2006.01)
*A61F 7/10* (2006.01)
(Continued)

(52) U.S. Cl.
CPC .............. *A61F 7/106* (2013.01); *A42B 1/008* (2013.01); *A61F 2007/0002* (2013.01);
(Continued)

(58) Field of Classification Search
CPC .............. A61F 7/106; A61F 2007/0002; A61F 2007/0007; A61F 2007/0012;
(Continued)

(56) References Cited

U.S. PATENT DOCUMENTS 3,429,315 A    2/1969  McDonald
4,138,743 A    2/1979  Elkins et al.
(Continued)

FOREIGN PATENT DOCUMENTS

CN    2179017 Y    10/1994
CN    202407260 U    9/2012
(Continued)

OTHER PUBLICATIONS

Halkey Roberts 840 Manual Inflator and rearm instructions 2015.
(Continued)

*Primary Examiner* — Kaitlyn E Smith
*Assistant Examiner* — Yasamin Ekrami
(74) *Attorney, Agent, or Firm* — Fox Rothschild LLP

(57) ABSTRACT

A thermal therapy headgear for a patient includes a plurality of thermal reaction compartments, a liquid chamber, a gas chamber, and a gas container. The thermal reaction compartments contain a first of at least two thermal reaction components, and the liquid chamber contains the second thermal reaction component. The gas container has therein a pressurized gas and a gas valve for selectively releasing the pressurized gas into the gas chamber. The gas in the gas chamber will apply pressure to the liquid chamber and force the second thermal reaction component through the valve and into the thermal reaction compartments to react and transfer heat with the patient, and the presence of the gas within the gas chamber will cushion the patient. A method for conducting hypothermic therapy is also disclosed.

13 Claims, 20 Drawing Sheets

(51) Int. Cl.
*A42B 1/008* (2021.01)
*A61F 7/00* (2006.01)

(52) U.S. Cl.
CPC .......... *A61F 2007/0007* (2013.01); *A61F 2007/0012* (2013.01); *A61F 2007/0056* (2013.01); *A61F 2007/0057* (2013.01); *A61F 2007/0096* (2013.01)

(58) Field of Classification Search
CPC ...... A61F 2007/0056; A61F 2007/0057; A61F 2007/0096; A61F 2007/0268; A61F 2007/0282; A61F 2007/0273; A61F 2007/0092; A42B 1/008
See application file for complete search history.

(56) References Cited

U.S. PATENT DOCUMENTS

| | | | |
|---|---|---|---|
| 4,382,446 A | 5/1983 | Truelock et al. | |
| 4,551,858 A | 11/1985 | Pastemack | |
| 4,742,827 A | 5/1988 | Lipton | |
| 4,753,241 A * | 6/1988 | Brannigan | A61F 7/02 156/210 |
| 4,753,242 A | 6/1988 | Saggers | |
| 4,765,338 A | 8/1988 | Turner et al. | |
| 4,776,042 A | 10/1988 | Hanson et al. | |
| 4,854,319 A | 8/1989 | Tobin | |
| 4,891,501 A | 1/1990 | Lipton | |
| 5,188,103 A | 2/1993 | Smith | |
| 5,274,865 A | 1/1994 | Takehashi | |
| 5,395,400 A | 3/1995 | Stafford et al. | |
| 5,539,934 A | 7/1996 | Ponder | |
| 5,950,234 A | 9/1999 | Leong et al. | |
| 6,183,501 B1 | 2/2001 | Latham | |
| 6,185,750 B1 | 2/2001 | Dumas | |
| 6,554,787 B1 | 4/2003 | Griffin et al. | |
| 7,083,839 B2 | 8/2006 | Fish et al. | |
| 7,930,772 B2 | 4/2011 | Fontanez | |
| 9,615,968 B2 | 4/2017 | Rand et al. | |
| 2003/0118779 A1 | 6/2003 | Fish et al. | |
| 2005/0034335 A1 | 2/2005 | Shows | |
| 2006/0005942 A1 | 1/2006 | Griesbach | |
| 2007/0150033 A1 | 6/2007 | Johnson et al. | |
| 2009/0198311 A1 | 8/2009 | Johnson et al. | |
| 2010/0037366 A1 | 2/2010 | Panicali | |
| 2010/0319110 A1 | 12/2010 | Preston-Powers | |
| 2010/0331752 A1 | 12/2010 | Cumming et al. | |
| 2012/0144555 A1 | 6/2012 | Panicali | |
| 2012/0151664 A1 | 6/2012 | Kirshon | |
| 2013/0041439 A1 | 2/2013 | Gallagher | |
| 2013/0152274 A1 | 6/2013 | Welch | |
| 2013/0172829 A1 | 7/2013 | Badawi | |
| 2013/0174332 A1 | 7/2013 | Bryant et al. | |
| 2013/0211484 A1 | 8/2013 | Rozental | |
| 2013/0331914 A1 | 12/2013 | Lee et al. | |
| 2014/0130239 A1 | 5/2014 | Preston-Powers | |
| 2014/0216061 A1 | 8/2014 | Paul | |
| 2014/0288624 A1 | 9/2014 | Wasko et al. | |
| 2014/0371828 A1 | 12/2014 | Whitely | |
| 2014/0379058 A1 | 12/2014 | Farrago et al. | |
| 2015/0297397 A1* | 10/2015 | Rand | A42B 1/22 607/110 |
| 2016/0030238 A1 | 2/2016 | Foster | |
| 2017/0209306 A1 | 7/2017 | Rand et al. | |
| 2020/0375793 A1* | 12/2020 | Dilligan | A61F 7/0085 |

FOREIGN PATENT DOCUMENTS

| | | |
|---|---|---|
| EP | 0585353 A1 | 3/1994 |
| WO | 2009095690 A1 | 8/2009 |

OTHER PUBLICATIONS

"Cooling helmets may stabilize stroke patients", Retrieved on Jan. 28, 2015, from <http://www.webmd.com/stroke/news/20040205/cooling-helmets-may-stabilize-stroke-patients> (3 pages).

"Diagram of Thermocrown", Retrieved on Jan. 28, 2015, from <http://www.thermopraxis.com/diagram.htm> (4 pages).

"Thermahelm", Retrieved on Jan. 28, 2015, from http://www.thermahelm.com/ (3 pages).

Thermopraxis: Our products, Retrieved on Jan. 28, 2015, from <http://www.thermopraxis.com/products.htm> (2 pages).

Extended European Search Report issued in EP Application No. 20197621.4 dated Feb. 19, 2021.

* cited by examiner

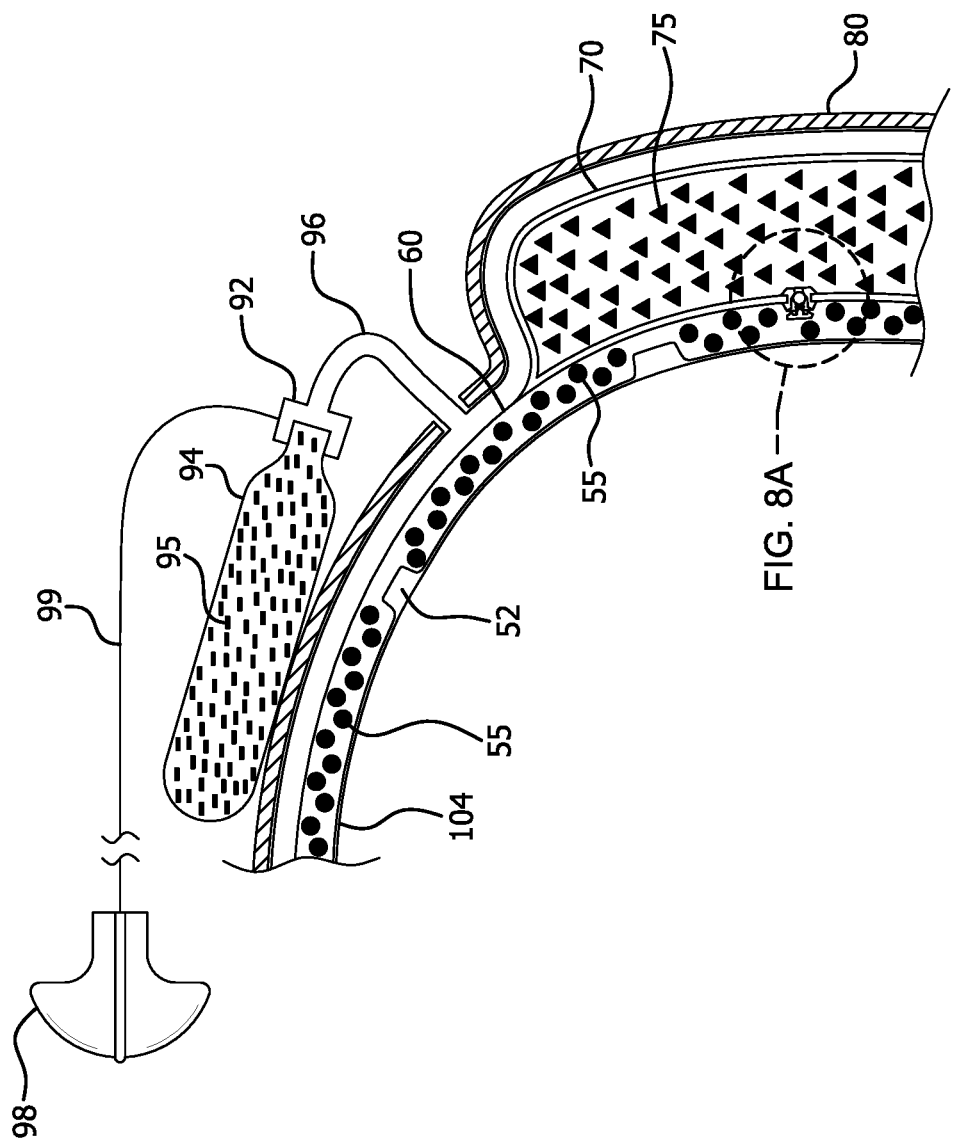

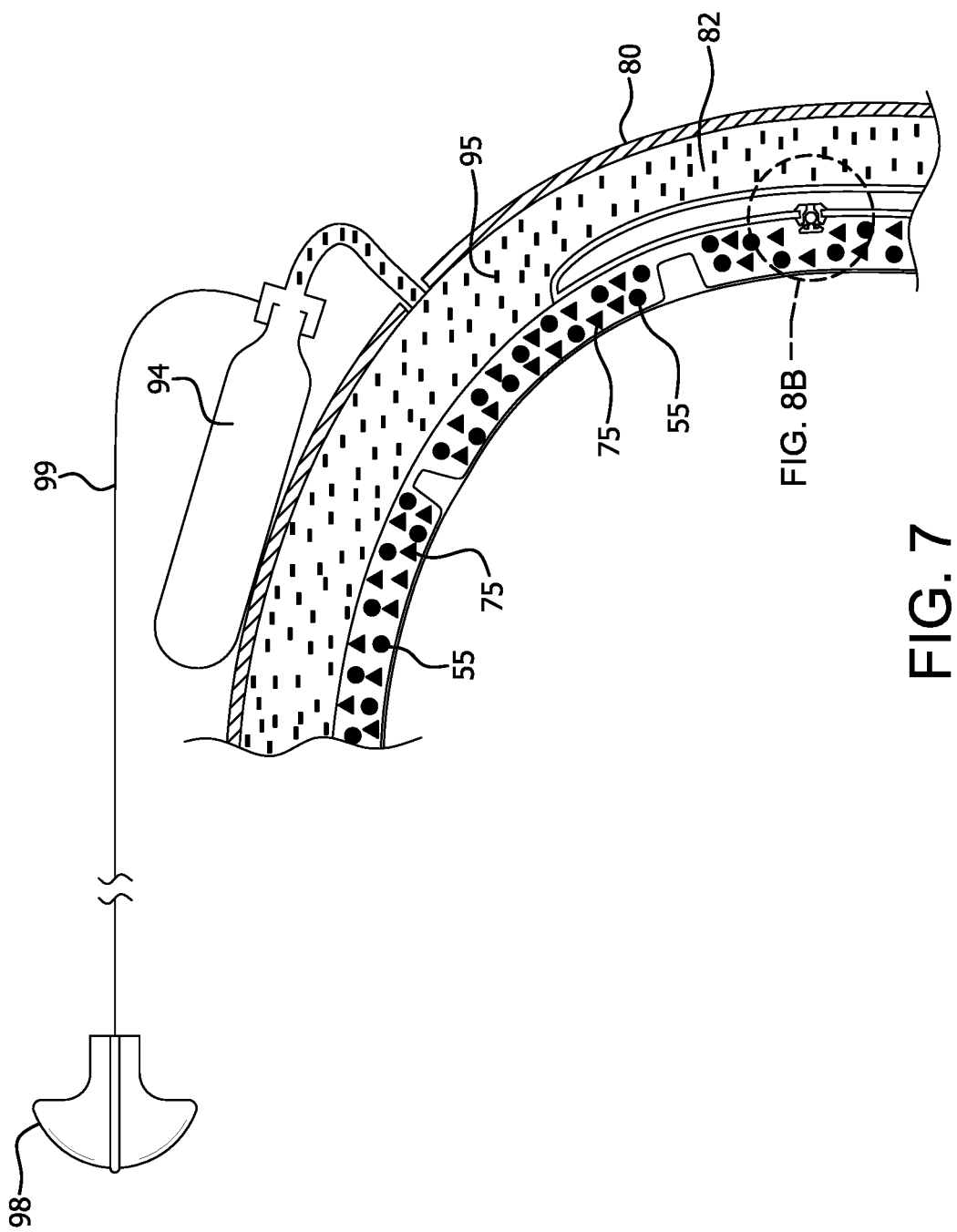

● : H₂O Port
↕ : H₂O Flow

PORTABLE THERMAL THERAPY AND SUPPORT APPARATUS FOR EMERGENCY MEDICAL TREATMENT

FIELD OF THE INVENTION

The present invention relates to the field of emergency medical treatment. More specifically the present invention relates to an emergency medical device for delivering thermal therapy and also support and cushioning to a patient as an emergency medical treatment.

BACKGROUND OF THE INVENTION

In recent years medical personnel have recognized in various emergency medical scenarios that irreparable damage to tissues of the brain and brainstem following oxygen deprivation, such as from cardiac arrest, stroke, or near-drowning, or alternatively from direct trauma, can be prevented and/or mitigated through rapid temperature reduction, known as therapeutic hypothermia or targeted temperature management. In other emergency medical scenarios, the application of heat is prescribed. Additionally, in numerous emergency medical scenarios proper positioning of the head of the patient is also of concern to open the airway of the patient for breathing and for optimal positioning for endotracheal intubation. Cushioning of the patient and particularly the point of injury can also be desirable. The current recommendation for therapeutic hypothermia is to initiate therapy as soon as possible after the event to optimally prevent brain damage.

There is shown in Rand et al, U.S. Pat. No. 9,615,968 (Apr. 11, 2017) a portable, rapid-cooling, hypothermia-inducing headgear apparatus for tissue preservation. The disclosure of this patent is hereby incorporated fully by reference. There remains a critical need for a thermal therapy device for emergency medical treatment that provides portable and on-demand therapy as well as patient positioning and/or cushioning. A significant issue in any portable apparatus is weight and size. This is especially an issue with current therapeutic hypothermia devices. Current devices are far too large and heavy to be used in a portable fashion at or nearest the point of injury. Previously suggested more portable methods of therapeutic hypothermia have been found to be either too invasive or were found to produce unwanted serious complications. Therefore, currently there is commonly a significant delay in initiating therapeutic hypothermia until a patient is transferred to a specialized unit in the hospital, which can be several hours after the initial injury. By this time, much irreversible damage has already occurred.

SUMMARY OF THE INVENTION

Thermal therapy apparatus for a patient includes a flexible base for conforming to the patient and a plurality of reaction compartments. Each compartment contains a first of at least two thermal reaction components. The thermal reaction compartments can be interconnected by fluid conduits. Each reaction compartment can be in thermal contact with a heat transfer surface for contacting the surface portion of the patient which will transfer heat to the patient. The thermal reaction components have an initial state where the thermal reaction components are separated from contact with each other, and a treatment state in which the thermal reaction components are placed into contact, wherein a thermal reaction takes place and transfers heat with the cooling surface and the corresponding portion of the patient.

A liquid chamber comprises a flexible wall and contains a second of the at least two thermal reaction components. The second thermal reaction component can be a liquid, and the liquid chamber can be connected to the fluid conduits by a valve. A gas chamber can adjoin the storage chamber. The gas container has therein a pressurized gas, and there can be a fluid connection between the gas container and the gas chamber, and a gas valve for selectively releasing the pressurized gas from the gas container through the fluid connection into the gas chamber;

Upon operation of the gas valve, pressurized gas will flow into the gas chamber and the gas in the gas chamber will apply pressure to the liquid chamber and force the second thermal reaction component through the valve and into the fluid conduits and thereby into the thermal reaction compartments. The at least two thermal reaction components will react and transfer heat with the heat transfer surface, and the presence of the gas within the gas chamber will support and cushion the patient.

The reaction compartments can be formed by a base and a cover. Portions of the base and the cover can be attached to form the reaction compartments and fluid conduit walls, and portions of the base and the cover can be unattached to form flexible fluid conduit channels. The cover can be attached to the base by RF welding, laser welding or adhesives. The thermal therapy the base and the cover can be flexible. The apparatus can comprise an elastomeric liner. The reaction compartments can be enclosed chambers connected by fluid conduits and secured to the elastic liner.

At least one of the thermal reaction components can include ammonium nitrate, and the other of the endothermic reaction components can include at least one selected from the group consisting of barium hydroxide and water. The thermal reaction components can provide an exothermic reaction to deliver heat to the patient, or an endothermic reaction to cool the patient.

The thermal therapy apparatus can further include a thermometer for providing an indication of the temperature of at least one of the cooling members. The thermal therapy apparatus can also include a timer. The timer can be activated by at least one selected from the group consisting of operation of the activation device and a temperature sensor. The thermal therapy apparatus can include a headpiece that can have earpieces for locating the headpiece on the users head. The headpiece can be constructed such that when the headgear is positioned on the head of the patients the thermal reaction compartments and the heat transfer surfaces will contact at least one pulse point of the patient. The the pulse points can be at least one selected from the group consisting of the forehead, the base of the neck, and the temples.

The liquid chamber can be an enclosed bag positioned between the reaction compartments and the gas chamber. The liquid chamber can include a fluid outlet communicating with the valve and the reaction compartments.

A method for administering thermal therapy to a surface portion of a patient can include the step of providing a thermal therapy device for a patient. The thermal therapy device includes a flexible piece for conforming to portion of the patient for receiving the thermal therapy, and a plurality of reaction compartments. Each reaction compartment contains a first of at least two thermal reaction components. The reaction compartments can be interconnected by fluid conduits. Each reaction compartment can be in thermal contact with a heat transfer surface for contacting the surface portion of the patient which will transfer heat with the surface portion of the patient. The thermal reaction components can have an initial state where the thermal reaction components are separated from contact with each other, and a treatment state in which the thermal reaction components are placed into contact, wherein a thermal reaction takes place and cools the cooling surface and the corresponding portion of the patient.

A liquid chamber can include a flexible wall and can contain a second of at least two thermal reaction components. The second thermal reaction component can be a liquid. The liquid chamber can be connected to the fluid conduits by a check valve. A gas chamber can adjoin the storage chamber. A gas container can have therein a pressurized gas, a fluid connection between the gas container and the gas chamber, and a gas valve for selectively releasing the pressurized gas from the gas container through the fluid connection into the gas chamber.

The method can include the step of operating the gas valve to place the thermal reaction components into contact with each other. Upon operation of the gas valve, pressurized gas will flow into the gas chamber and the gas in the gas chamber will apply pressure to the liquid chamber and force the second thermal reaction component through the check valve and into the fluid conduits and thereby into the reaction compartments. The at least two thermal reaction components will react and transfer heat between the thermal reaction compartments and the heat transfer surface. The presence of the gas within the gas chamber will cushion the surface portion of the patient.

BRIEF DESCRIPTION OF THE DRAWINGS

There are shown in the drawings embodiments that are presently preferred it being understood that the invention is not limited to the arrangements and instrumentalities shown, wherein:

FIG. 6 is a magnified view of the schematic cross-section and in the mode of operation of FIG. 4.

FIG. 7 is a magnified view of the schematic cross-section in the mode of operation of FIG. 5.

DETAILED DESCRIPTION OF THE INVENTION

Figure 2:
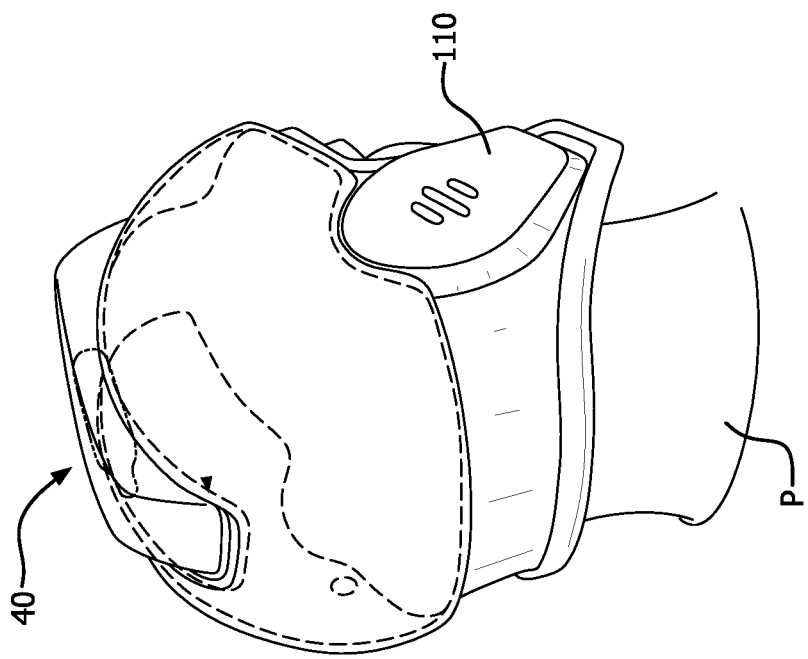
FIG. 2 is a rear perspective view, partially in phantom.

Thermal therapy apparatus according to the invention can include a flexible base for conforming to a portion of the patient. The base can be in the form of a headgear for a patient, comprising a flexible headpiece conforming to the head of the patient for engaging the head of the patient. A plurality of thermal reaction compartments can be provided, each compartment containing a first of at least two endothermic reaction components. The reaction compartments can be interconnected by fluid conduits. Each reaction compartment can be in thermal contact with a heat transfer surface for contacting the surface portion of the patient which will transfer heat with the head or corresponding body part of the patient. The thermal reaction components have an initial state where the thermal reaction components are separated from contact with each other, and a treatment state in which the thermal reaction components are placed into contact, wherein an endothermic or exothermic reaction takes place and cools or heats, respectively, the heat transfer surface and the corresponding portion of the patient.

A liquid chamber includes a flexible wall and contains a second of the at least two thermal reaction components. The second thermal reaction component is a liquid or contained within a liquid. The liquid chamber can be connected to the fluid conduits by a valve which prevents the flow of liquid into the thermal reaction compartments until operation of the apparatus is desired.

A gas chamber adjoins and/or surrounds the liquid chamber. A gas container can have therein a pressurized gas. There is a fluid connection between the gas container and the gas chamber. A gas valve can be provided for selectively releasing the pressurized gas from the gas container through the fluid connection into the gas chamber.

Upon operation of the gas valve, pressurized gas will flow into the gas chamber and the gas in the gas chamber will apply pressure to the liquid chamber, and particularly the flexible wall. This pressure will force the second thermal reaction component through the valve and into the fluid conduits and thereby into the reaction compartments, where the at least two thermal reaction components will react endothermically or exothermically and transfer heat between the thermal reaction compartments and the heat transfer surface and the corresponding part of the patient in contact with the cooling surface. At the same time, the presence of the gas within the gas chamber will provide a cushioning effect that will support and/or cushion the head or corresponding body part of the patient to which the apparatus is attached.

The thermal reaction compartments can be provided in different constructions. In one embodiment, the thermal reaction compartments are formed by a base and a cover. Portions of the base and the cover can be attached to form the reaction compartments and fluid conduit walls. Other portions of the base and the cover can be unattached to form fluid conduit channels (thus avoiding rigid tubes which would impede flexibility of the device and appropriate fit to the patient). The cover can be attached to the base by any suitable process, including radio frequency (RF) welding, adhesives and the like. The base and the cover can be flexible, to allow adaptation to the patient and to provide ease of packaging and storage.

The thermal therapy apparatus can include an elastomeric liner. The elastomeric liner allows the thermal therapy components to remain in contact with the head or other corresponding body part of the patient to prevent air gaps which would insulate and prevent proper heat transfer between the heat transfer surface and the patient. The thermal reaction compartments can be enclosed chambers or bladders connected by fluid conduits and secured to the elastomeric liner.

The heat transfer surface is positioned to transfer heat from a thermal reaction compartment to a desired part of the patient. The heat transfer surface can be a part of the thermal reaction compartment that faces the patient, or a part of an elastomeric liner between the thermal reaction compartment and the patient. The heat transfer surface can also be a dedicated heat transfer component, such as from a material that has an enhanced heat transfer capability, and is positioned in the apparatus so as to conduct heat between the thermal reaction compartment and the patient when the apparatus is in use.

The thermal reaction components can be any of several possible reaction components which react endothermically or exothermically. In one embodiment, one of the thermal reaction components can comprise ammonium nitrate, and the other of the endothermic reaction components can comprise water. Barium hydroxide also reacts endothermically with ammonium nitrate and can be used. Other combinations are possible. One of the thermal reaction components can be a liquid for storage in the liquid compartment. The other of the thermal reaction components that is stored in the thermal reaction compartments can be a fluid or a solid. Exothermic thermal reaction components can also be used. Many different such exothermic reaction components are known and can be used.

The thermal therapy apparatus of the invention can include integrated devices useful for emergency medical treatment. For example, a thermometer can be provided for providing an indication of the temperature of at least one of the cooling members. A timer can be provided and can be activated by at least one selected from the group consisting of operation of the activation device and a temperature sensor.

The temperature attained by the thermal therapy apparatus can vary. The temperature will in part depend on the nature and quantity or concentration of thermal reaction components. The temperature experienced by the patient will also depend on the heat transfer characteristics of the thermal reaction compartments and heat transfer surface, such as material composition and thickness. For example, in one embodiment the endothermic reaction components cool the heat transfer surface to a temperature of less than 15° C. when activated.

The thermal therapy apparatus can be thermal therapy headgear, and can include earpieces for locating the headpiece on the users head. The thermal reaction compartments can be positioned on the headgear such that when the headgear is positioned on the head of the patients the thermal reaction compartments and the associated heat transfer surfaces will contact anatomical parts of the head corresponding to the brain or alternatively at least one pulse point of the patient. The pulse points can include at least of the forehead, the base of the neck, and the temples. There are known pulse points elsewhere on the body and the apparatus can be adapted to apply thermal therapy to an intended location.

The liquid chamber can be of any suitable construction. The liquid chamber can be an enclosed bag positioned between the thermal reaction compartments and the gas chamber. The liquid chamber can include a fluid outlet communicating with a one-way valve and the thermal reaction compartments. The liquid chamber can alternatively be formed as a chamber formed by joining edges of adjacent layers to form an enclosed chamber.

A method for administering hypothermic therapy to a surface portion of a patient can include providing a thermal therapy device for a patient comprising a flexible piece for conforming to portion of the patient for receiving the thermal therapy. A plurality of thermal reaction compartments each contain a first of at least two endothermic reaction components. The thermal reaction compartments are interconnected by fluid conduits. Each thermal reaction compartment is in thermal contact with a heat transfer surface which will transfer heat with the surface portion of the patient.

A liquid chamber includes a flexible wall and contains a second of at least two endothermic reaction components, the second endothermic reaction component being a liquid. The liquid chamber can be connected to the fluid conduits by a valve. A gas chamber adjoins the liquid chamber. The gas chamber does not have to be immediately adjacent to the liquid chamber but it is a convenient construction. A gas container has therein a pressurized gas, and there is a fluid connection between the gas container and the gas chamber. A gas valve is provided for selectively releasing the pressurized gas from the gas container through the fluid connection into the gas chamber.

The gas valve is operated to place the endothermic reaction components into contact with each other, wherein upon operation of the gas valve, pressurized gas will flow into the gas chamber and the gas in the gas chamber will apply pressure to the liquid chamber and force the second endothermic reaction component through the check valve and into the fluid conduits and thereby into the reaction compartments, where the at least two endothermic reaction components will react and transfer with a portion of the patient, and the presence of the gas within the gas chamber will cushion and support the patient.

While the thermal reaction is described as endothermic as many emergency medical protocols require such therapy, it is also possible that the endothermic reaction could be negative, or exothermic. In this embodiment, the reaction components would generate therapeutic heat. Many medical protocols call for the application of heat to a patient, and the invention can be adapted for use in such protocols to apply heat and also cushion the patient on demand.

There is shown in FIGS. 1-13 thermal therapy apparatus 40 in the form of a headpiece. The headpiece 40 is dimensioned to fit over the head of the patient P. As shown particularly in FIG. 3, the headpiece 40 can be comprised of several parts or layers. A thermal reaction compartment layer 44 can be formed with a multitude of thermal reaction compartments 48 formed therein. The thermal reaction compartments 48 can be formed by any suitable means, such as by injection molding or thermoforming depressions or wells in the thermal reaction compartment layer 44 leaving raised ridges or walls 52.

Liquid flow conduits 56 can be provided between the thermal reaction compartments 48 by suitable means. In one embodiment, a thermal reaction compartment cover 60 is adhered to walls 52 by suitable means such as radio frequency (RF) welding, laser welding, or adhesives. This will enclose the thermal reaction compartments 48. The cover 60 is not adhered to the walls 52 at conduit locations 56, such that upon the application of fluid pressure the cover 60 will lift from the wall 52 to allow fluid to flow through the conduit 56 so formed.

A liquid chamber 70 is provided to store one of the thermal reaction components in liquid form. The liquid chamber 70 can be in different forms, but as shown is formed in a substantially U-shape leaving a central opening 78 to provide a space for a gas canister assembly to be described. A liquid conduit 74 communicates with the valve 76 and a liquid conduit 64 can communicate with the thermal reaction compartment cover 60 and thermal reaction compartments 48.

A gas chamber 82 is provided to receive gas from the gas canister assembly. The gas chamber 82 can take different forms. In one embodiment, the gas chamber is formed by the gas chamber cover 80 being hermetically sealed to lower edges 81 of the thermal reaction compartment layer 44. The liquid chamber 70 can be secured within the space between the gas chamber 80 and the cover 60 of the thermal reaction compartment layer 44. The liquid compartment 70 can be fixed in place as by RF welding, laser welding, or adhesives, or can be free-floating in the gas chamber 82 in the space between the gas chamber cover 80 and the thermal reaction compartment cover 60 of the thermal reaction compartment layer 44. An opening 84 can be provided to receive gas from the gas canister assembly into the gas chamber 80. The opening 84 can include a one-way valve.

The gas canister assembly can take different forms. In one embodiment the gas canister assembly includes a gas canister body 90 adapted to receive gas canister 94. Actuators such as pull tabs 98 and pull cord 99 can also be provided. Operation of the gas canister assembly can be by suitable means and are effective to release a pressurized gas from the gas canister 94 into the gas chamber 80. A protective cover 100 can be positioned over the gas canister assembly. The gas in the canister 94 can be air or another suitable pressurized gas.

Figure 1:
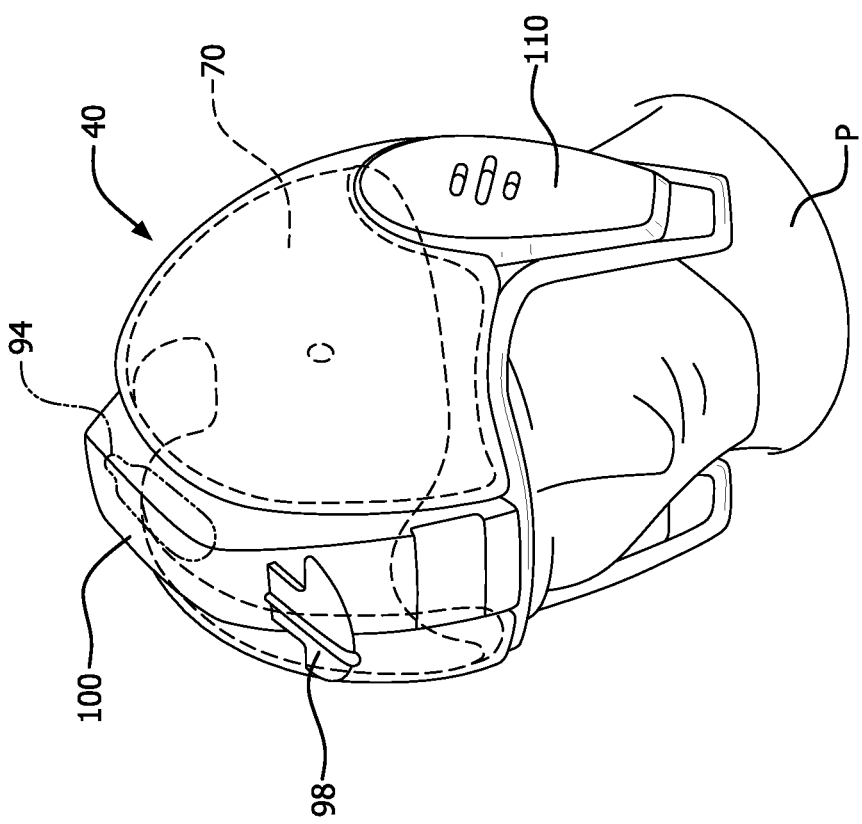
FIG. 1 is a front perspective view of a thermal therapy apparatus according to the invention, partially in phantom, on the head of a patient.
Figure 3:
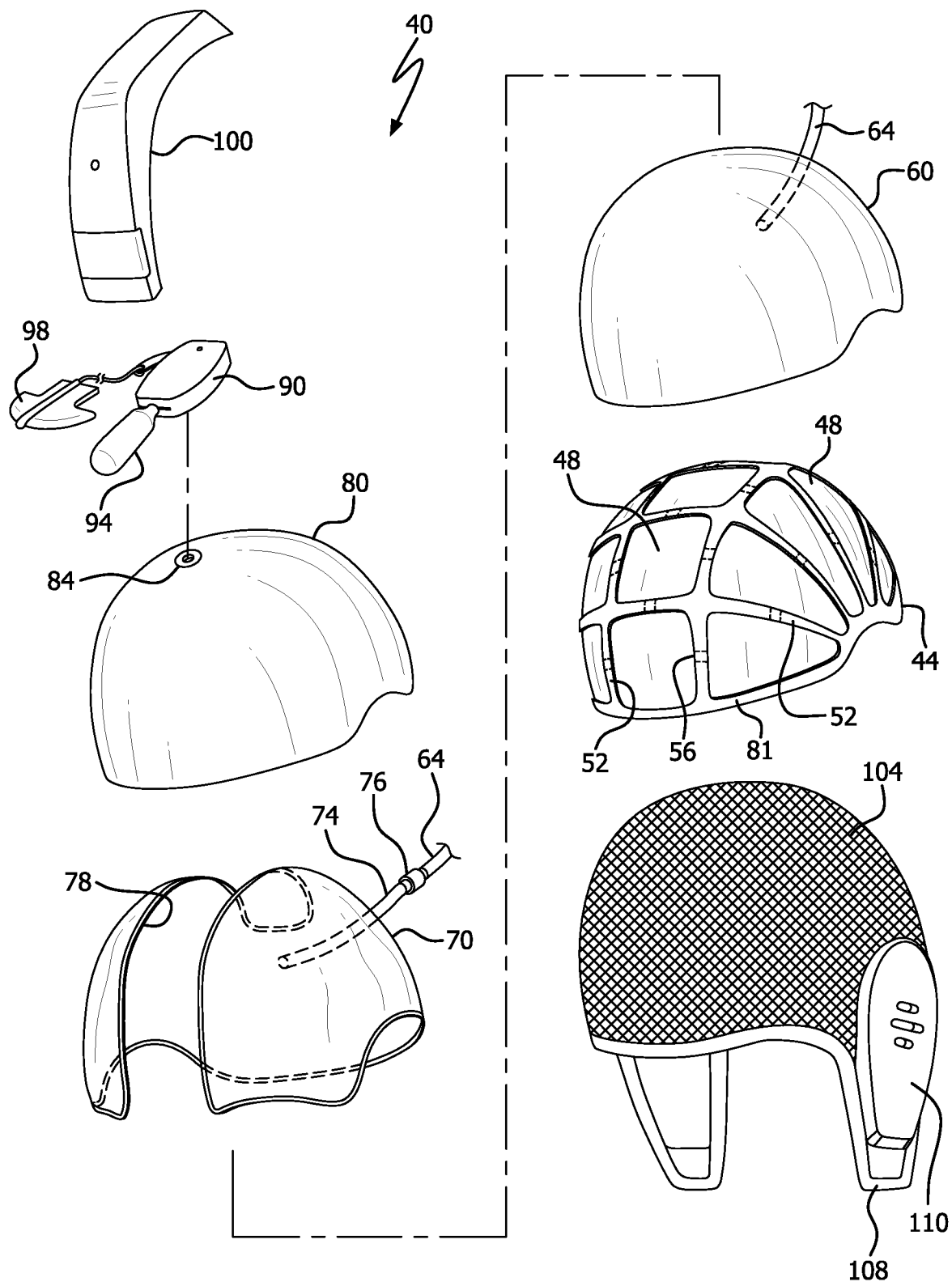
FIG. 3 is an exploded perspective view of a thermal therapy apparatus according to the invention.
Figure 4:
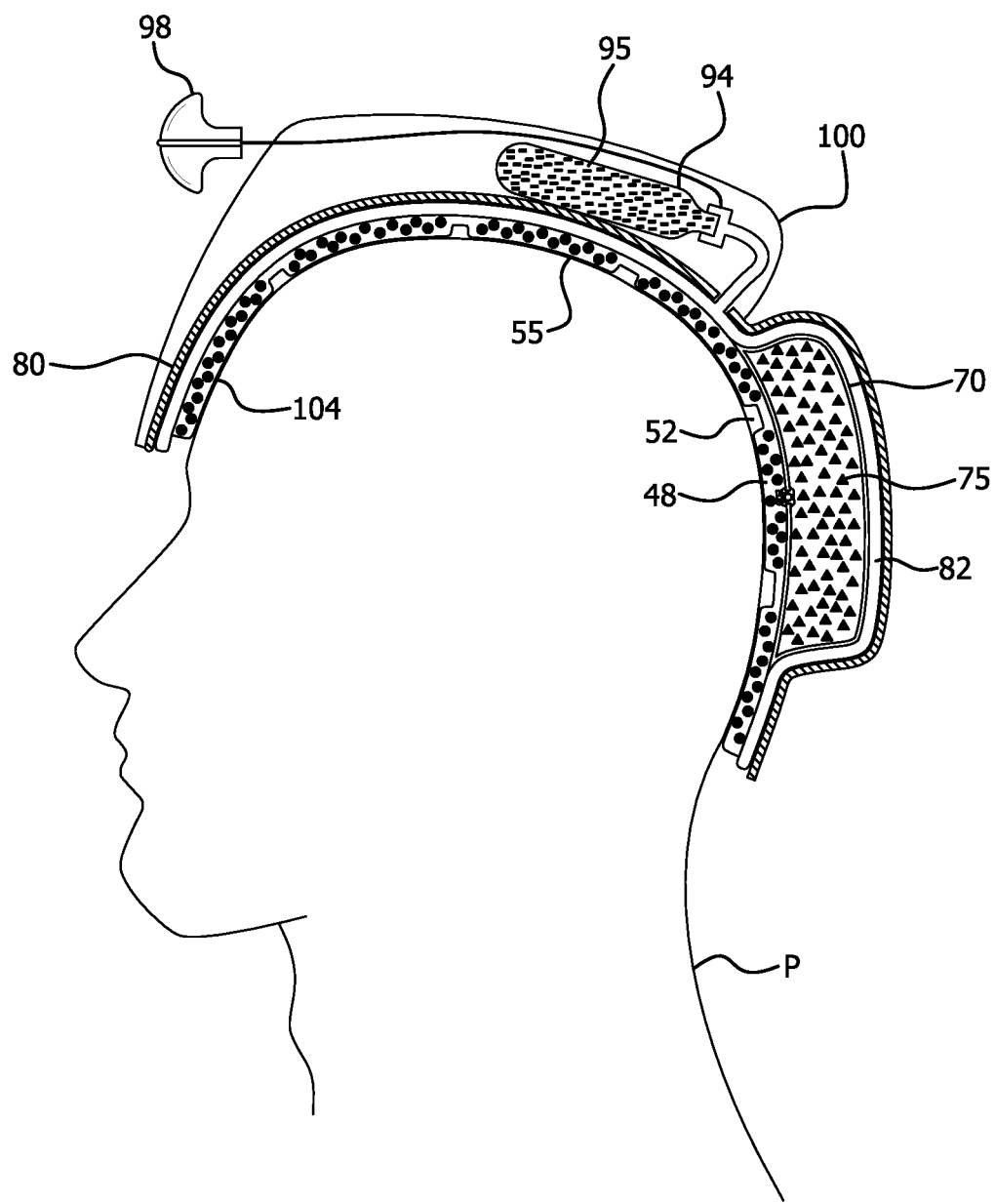
FIG. 4 is a schematic cross-section of the apparatus in a first mode of operation.

It is desirable that the thermal reaction compartments 48 are properly positioned relative to the head of the patient. A flexible base such as elastomeric liner 104 can be provided for this purpose. The elastomeric liner stretches to conform to the head of the patient, ensuring that no air gaps are formed between the liner and the head of the patient. Air gaps would cause an insulating effect which would interfere with heat transfer from the thermal reaction compartment 68 to the patient P. The liner also allows for good fit over various head sizes. Ear flaps 108 and earpieces 110 can be provided to further assist in positioning and retaining the headpiece 40 properly on the head of the patient (FIGS. 1-2).

Operation of the thermal therapy apparatus begins at an initial state (FIG. 4, FIG. 6) wherein one of the thermal reaction components such as ammonium nitrate 55 is provided in the thermal reaction compartments 48. Another of the thermal reaction components in liquid form, such as water 75, is provided in the liquid chamber 70. Pressurized gas 95 is provided in the gas canister 94. The gas chamber 82 is initially substantially empty.

Figure 5:
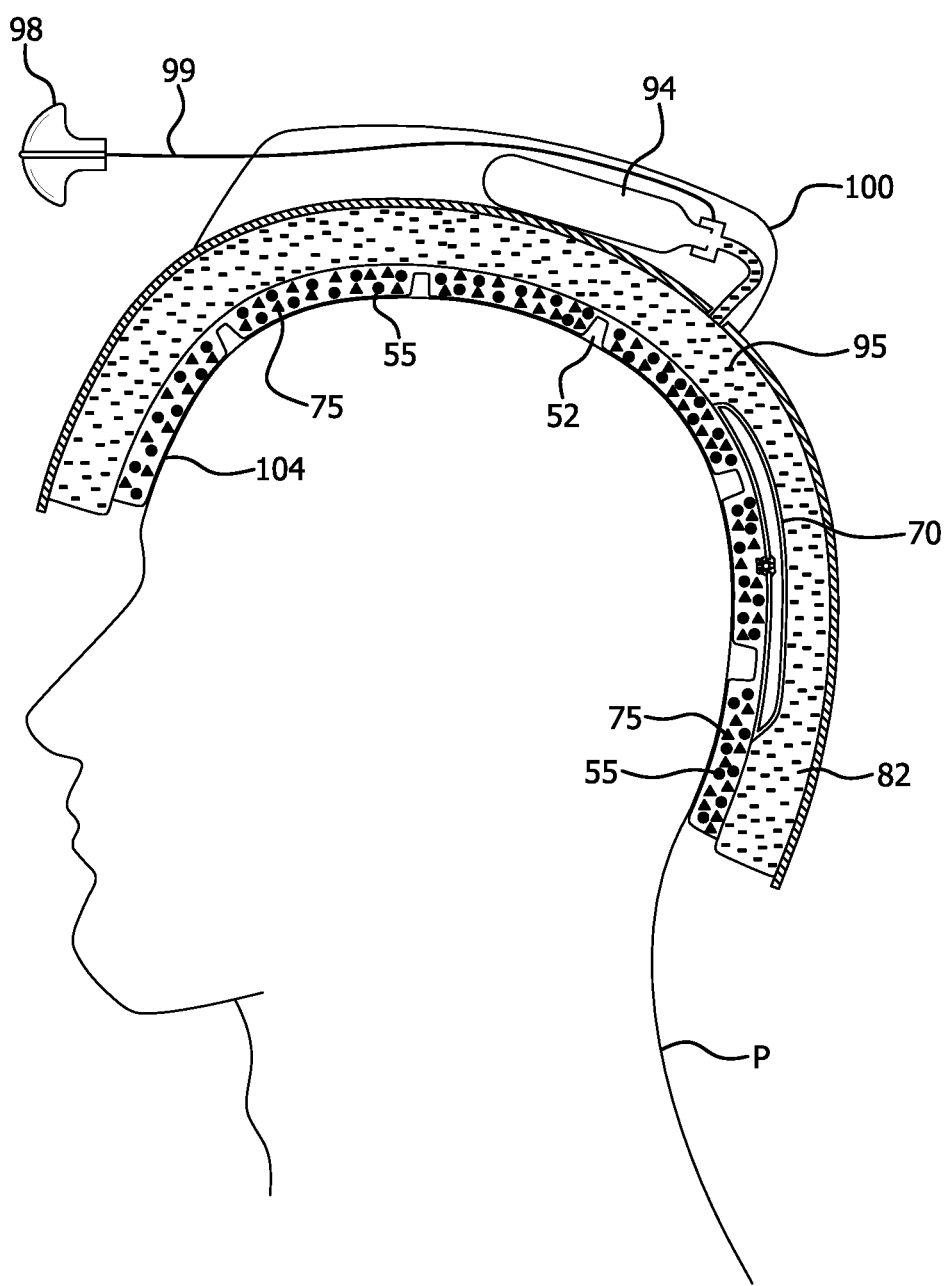
FIG. 5 is a schematic cross-section of the apparatus in a second mode of operation.

Upon manipulation of the pull tab 98 and pull cord 99, gas 95 is released from the gas canister 94 through canister body 92 and gas conduit 96 (FIG. 5, FIG. 7). Gas 95 fills the gas chamber 82. This applies pressure to the flexible liquid chamber 70. Water 75 is forced from the liquid chamber 70 into one or more of the thermal reaction compartments 48. Water 75 is dispersed through conduits 56 into the other thermal reaction compartments 48. In the thermal reaction compartments 48 the thermal reaction components mix and react endothermically or exothermically to affect heat transfer with the patient. Heat transfer with the patient is affected through a heat transfer surfaces in communication with the patient. The heat transfer surface can be an outside wall of the thermal reaction compartments 48 adjacent to the patient, or through conduction the heat transfer surface can be a portion of the elastomeric liner 104. The heat transfer surfaces can also be a dedicated high thermal conductivity material provided in the elastomeric liner 104 or the thermal reaction compartment layer 44. Other constructions are possible.

Figure 8A:
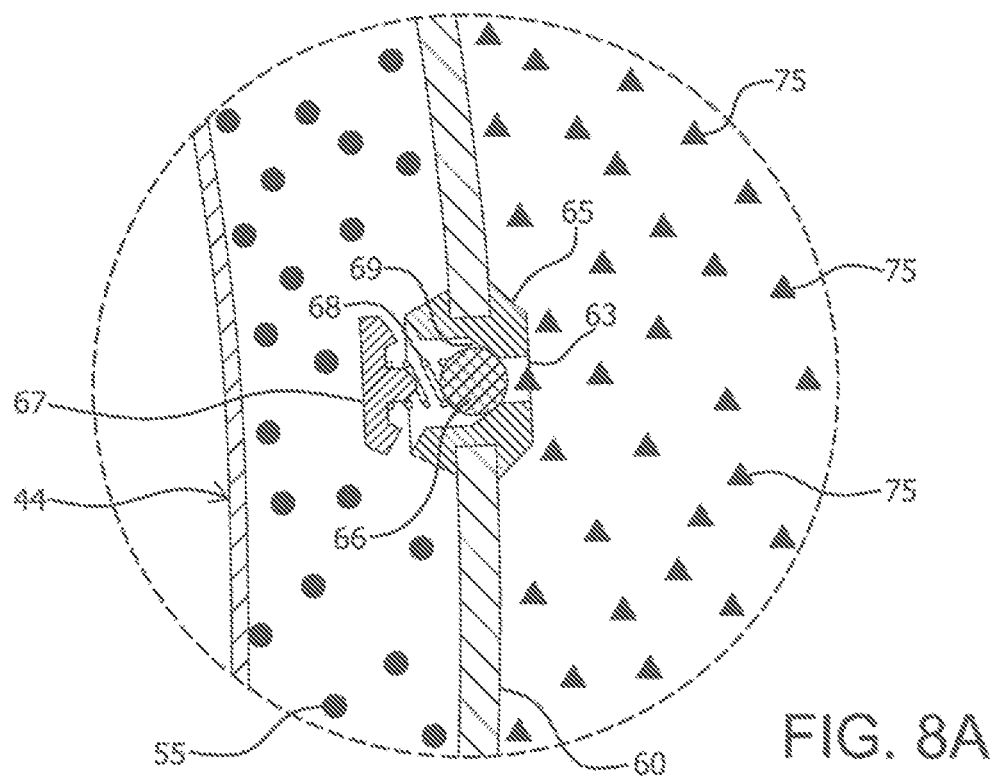
FIG. 8A is a magnified view of valve area 8A in the mode of operation of FIG. 6.
Figure 8B:
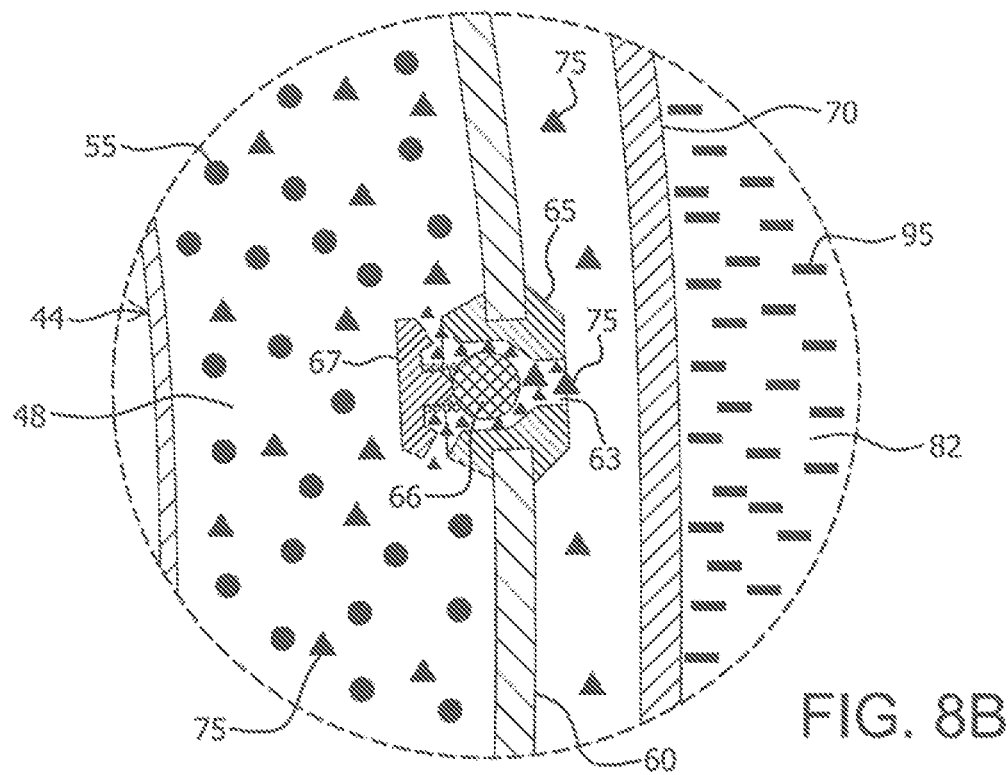
FIG. 8B is a magnified view of valve area 8B in the mode of operation of FIG. 7.

A one-way or check valve is provided between the liquid chamber 70 and the reaction compartments 48 to prevent backflow of reactants or reactive products from the thermal reaction compartments 48 into the liquid chamber 70. Such a valve is shown in FIG. 8A and FIG. 8B. The valve can include a valve body 65 having a valve passage 63. A valve ball 66 is operable to open and close the valve passage 63. A spring 68 is positioned between the valve ball 66 and a valve disk 67 which includes a spring seat. In an initial condition shown in FIG. 8A, the valve ball 66 is urged by spring 68 against valve ball seat 69 to close passage 63. Upon the introduction of pressurized gas 95 into the gas chamber 82 as shown in FIG. 8B, water 75 is forced through the valve passage 63 and the pressure acts upon valve ball 66 against spring 68 to open the flow passage 63 to the flow of water 75.

Figure 9:
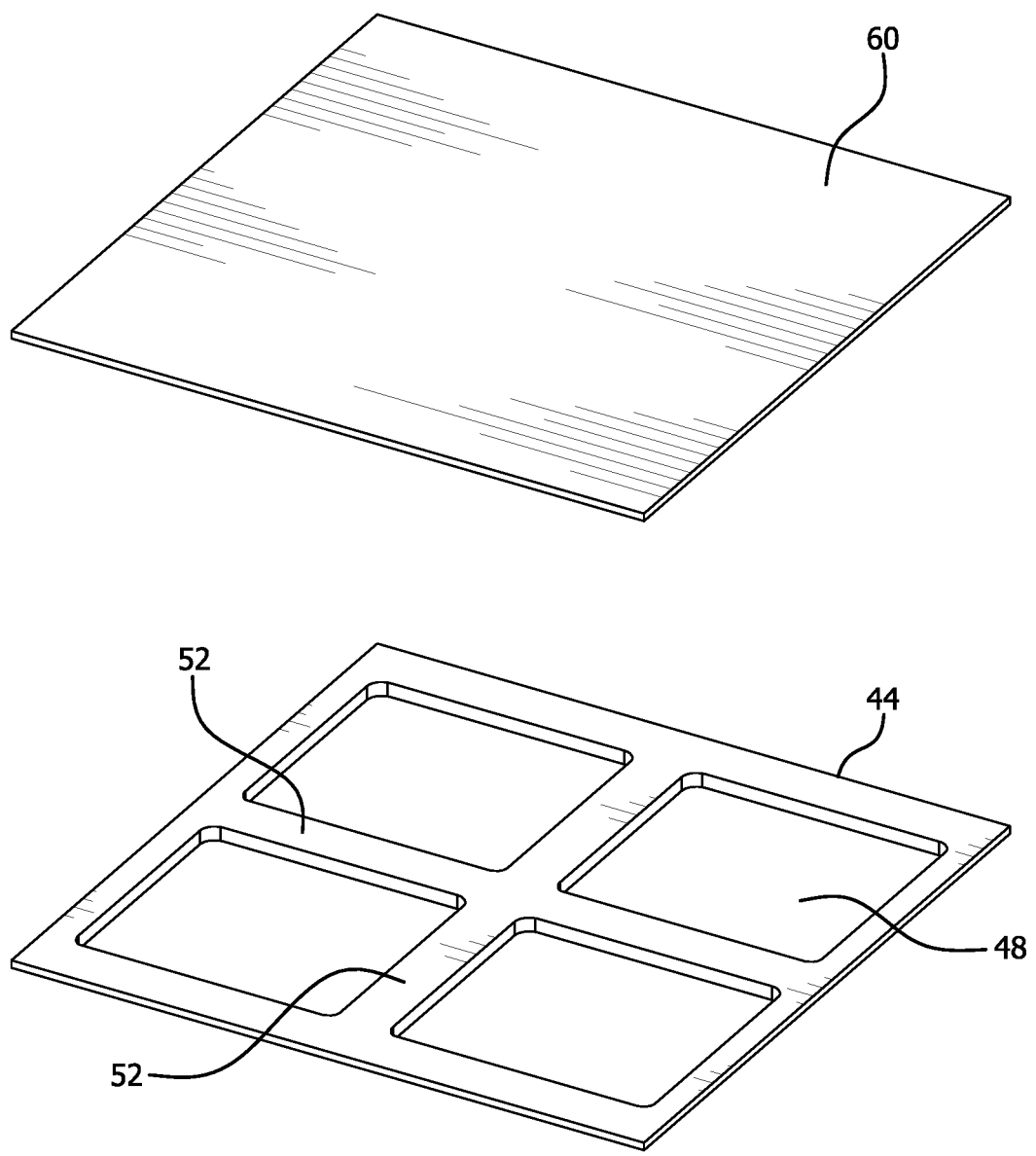
FIG. 9 is an exploded perspective of thermal reaction compartments.

Operation of the thermal reaction compartments is particularly shown in FIGS. 9-13. The thermal reaction compartment layer 44 includes thermal reaction compartments 48 with raised compartment walls 52 and cover 60 (FIG. 9).

Figure 10:
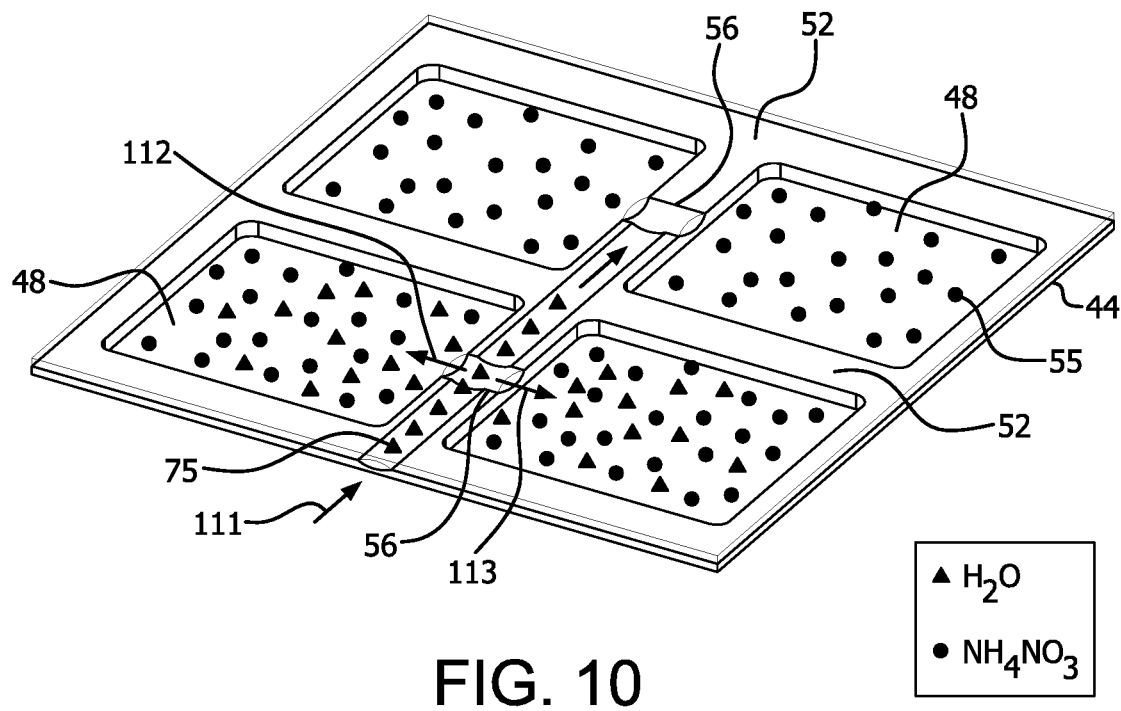
FIG. 10 is a schematic perspective of thermal reaction compartments, in a first mode of operation.
Figure 11:
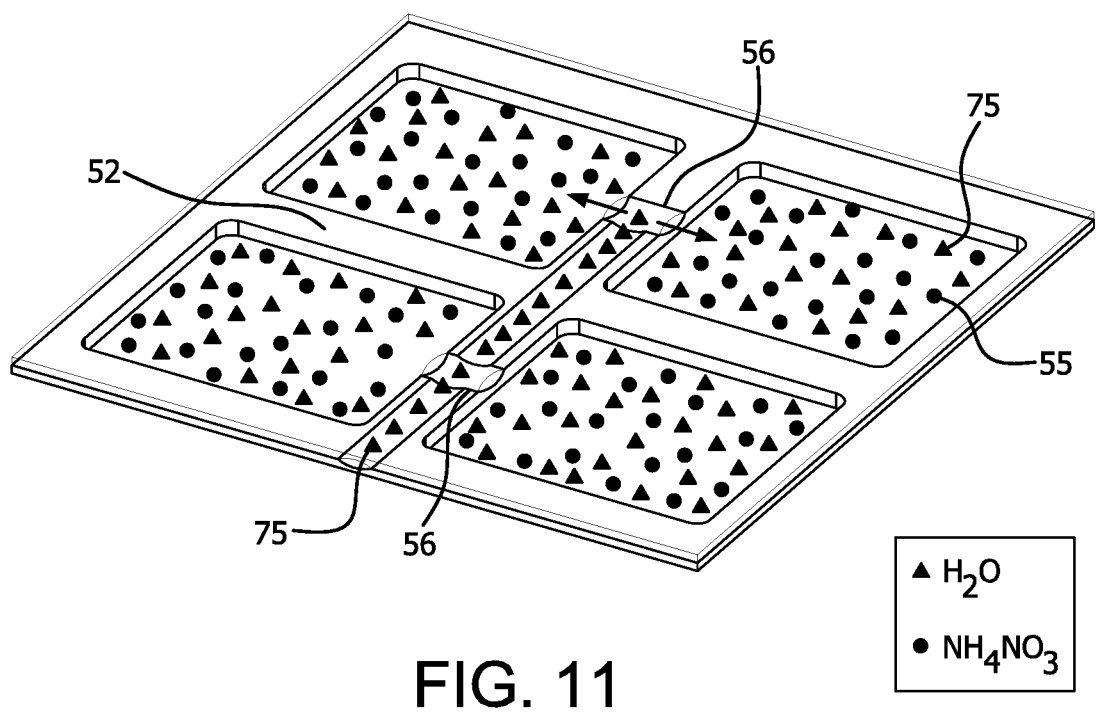
FIG. 11 is a schematic perspective of thermal reaction compartments, in a second mode of operation.
Figure 12:
FIG. 12 is a schematic cross-section of a liquid flow channel, in a first mode of operation.
Figure 13:
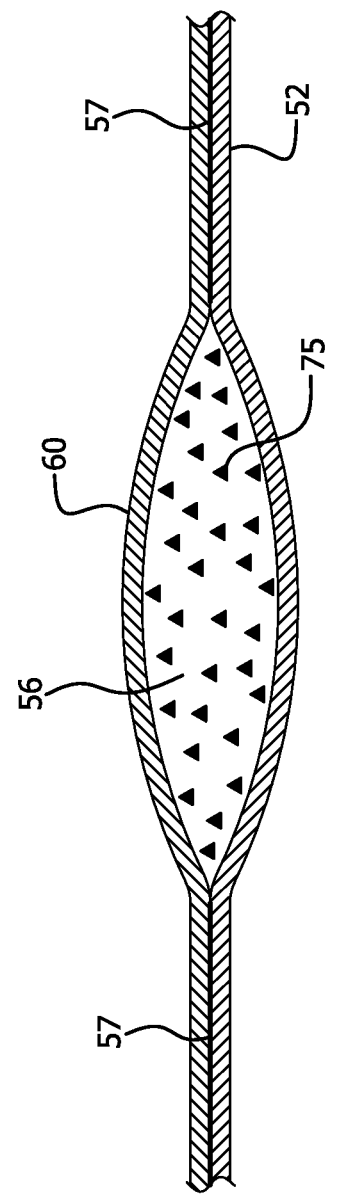
FIG. 13 is a schematic cross-section of a liquid flow channel, in a second mode of operation.
Figure 15:
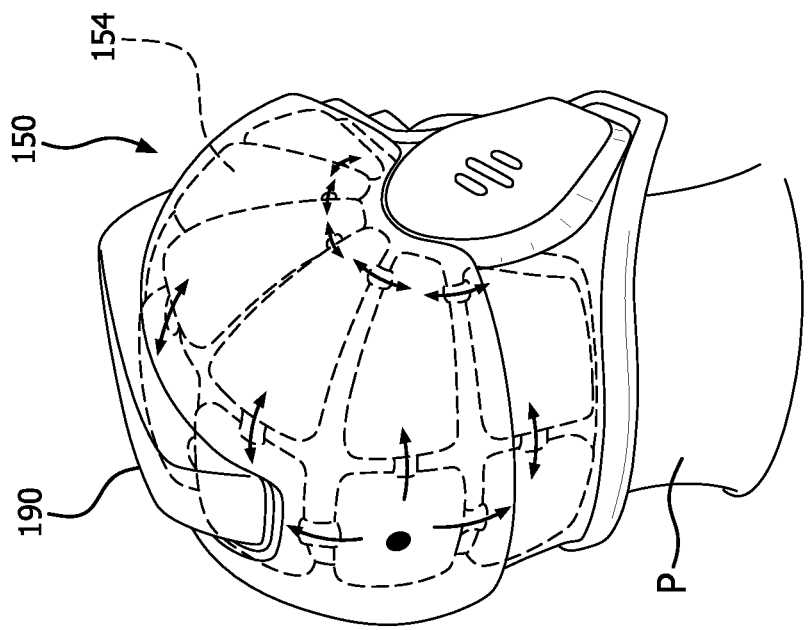
FIG. 15 is a rear perspective view, partially in phantom.
Figure 14:
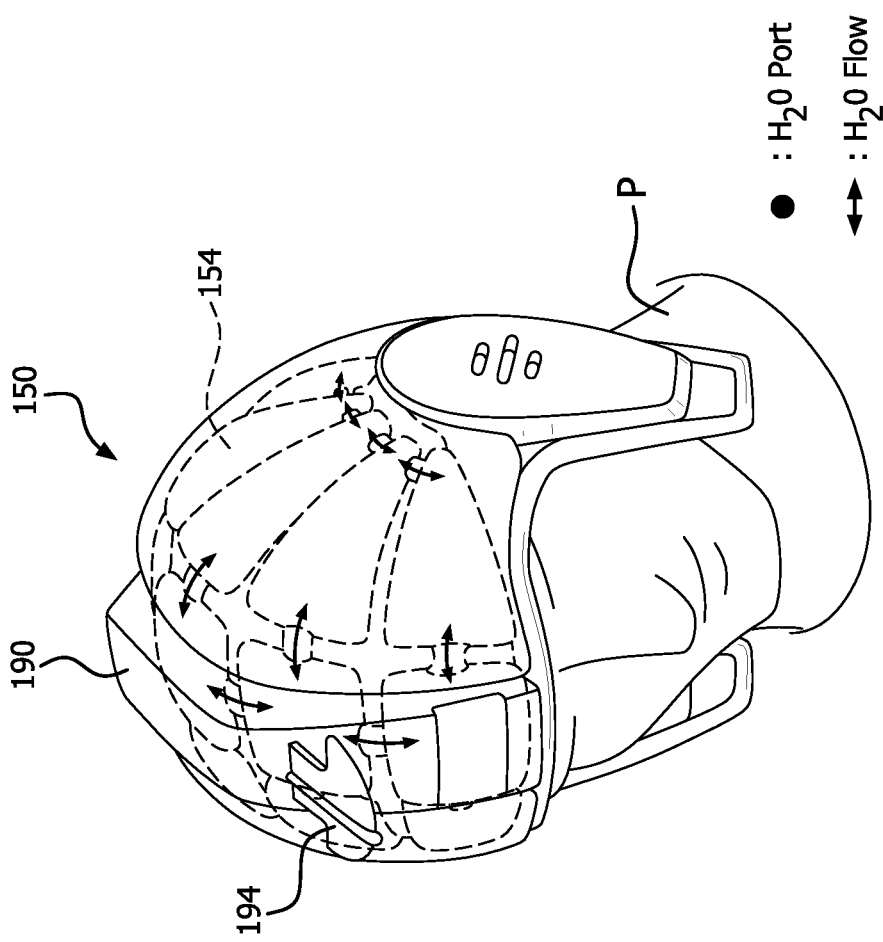
FIG. 14 is a front perspective view, partially in phantom, of an alternative embodiment of thermal therapy apparatus according to the invention on the head of a patient.

As shown in FIG. 10, as water 75 enters in the direction shown by arrow 111 it moves through liquid conduits 56 into the thermal reaction compartments 48 as shown by arrows 112 and 113. As shown in FIG. 11, the water 75 mixes with ammonium nitrate 55 and undergoes a chemical reaction which can be exothermic or endothermic. FIGS. 12-13 show how gaps in adhesion between the walls 52 and cover 60 of the thermal reaction compartment layer 44 can result in flow conduits 56. The adhered areas 57 prevent liquid flow, while the area in between the adhered areas 57 form a potential flow channel 56. As water 75 is forced into the reaction compartments 48, the pressure of the water 75 forces the cover 60 from the wall 52 in areas where the cover 60 is not secured to the wall 52, forming a flow conduit 56 (FIG. 13). Other constructions are possible.

Figure 17:
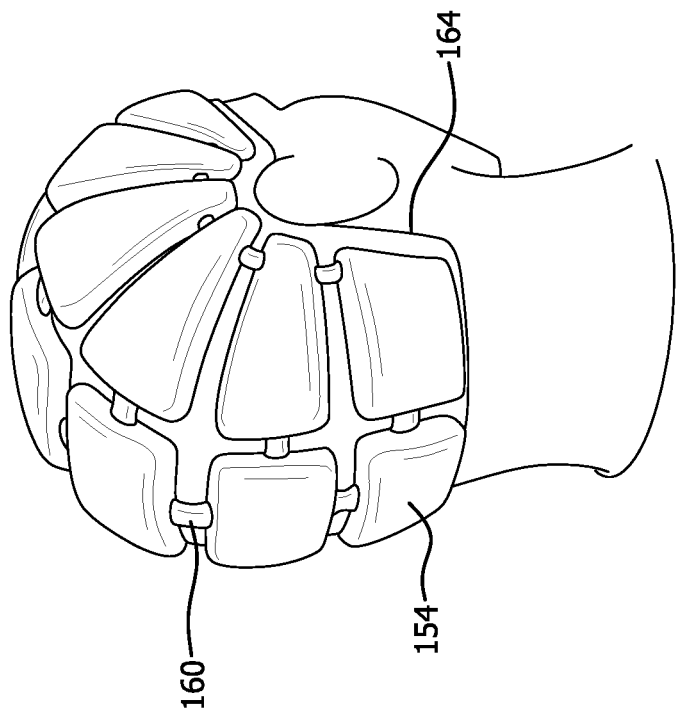
FIG. 17 is a rear perspective of thermal reaction compartments of the alternative embodiment with outer layers removed.
Figure 16:
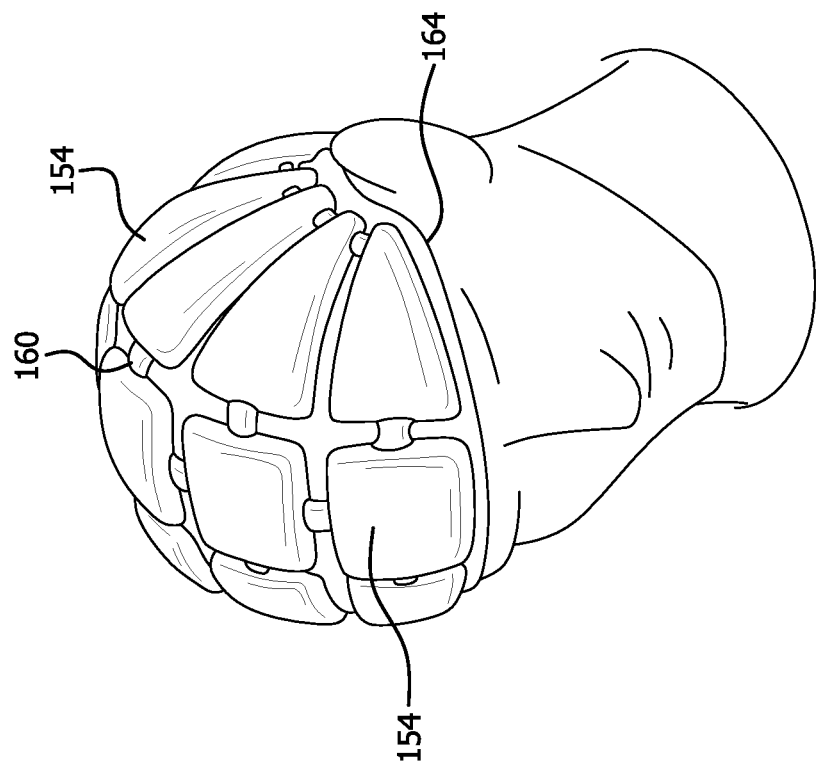
FIG. 16 is a front perspective view of thermal reaction compartments of the alternative embodiment illustrated with outer layers removed for understanding.
Figure 19:
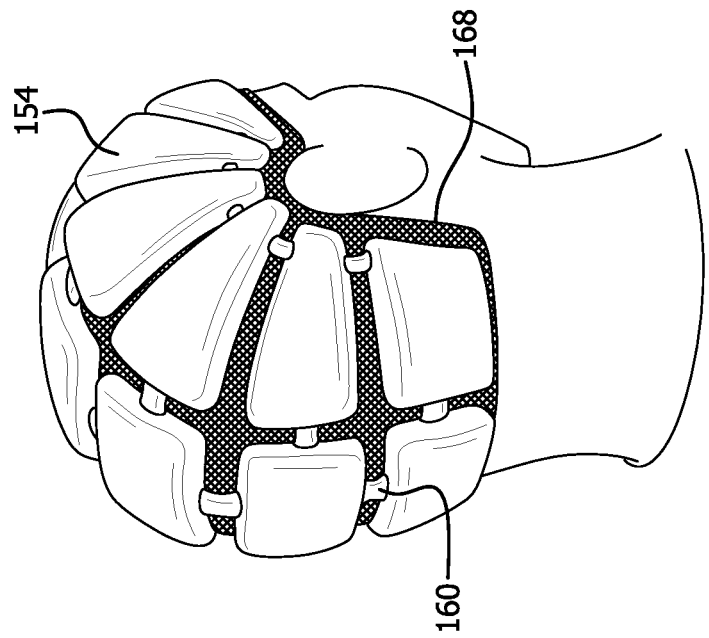
FIG. 19 is a rear perspective view of thermal reaction compartments on an elastomeric liner.
Figure 18:
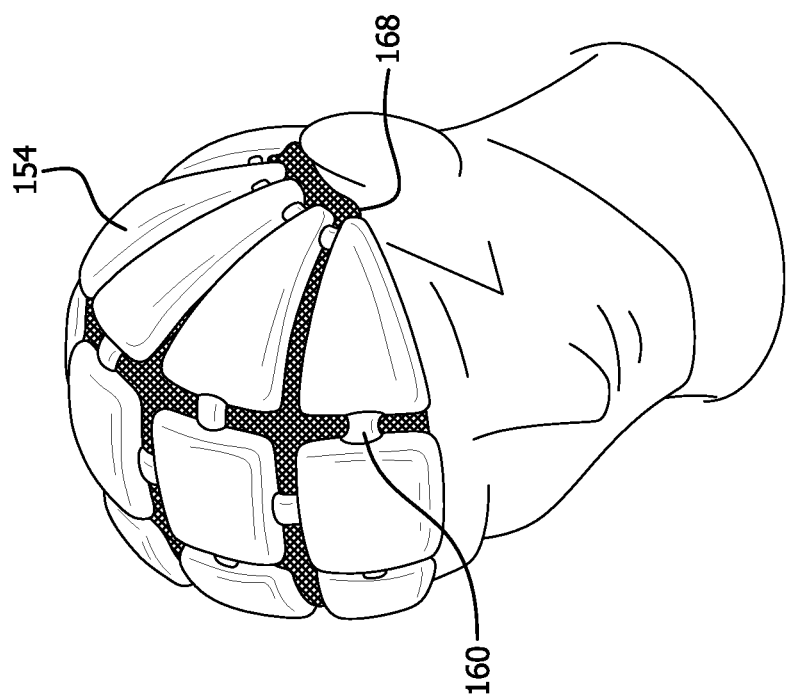
FIG. 18 is a front perspective view of thermal reaction compartments on an elastomeric liner.
Figure 20:
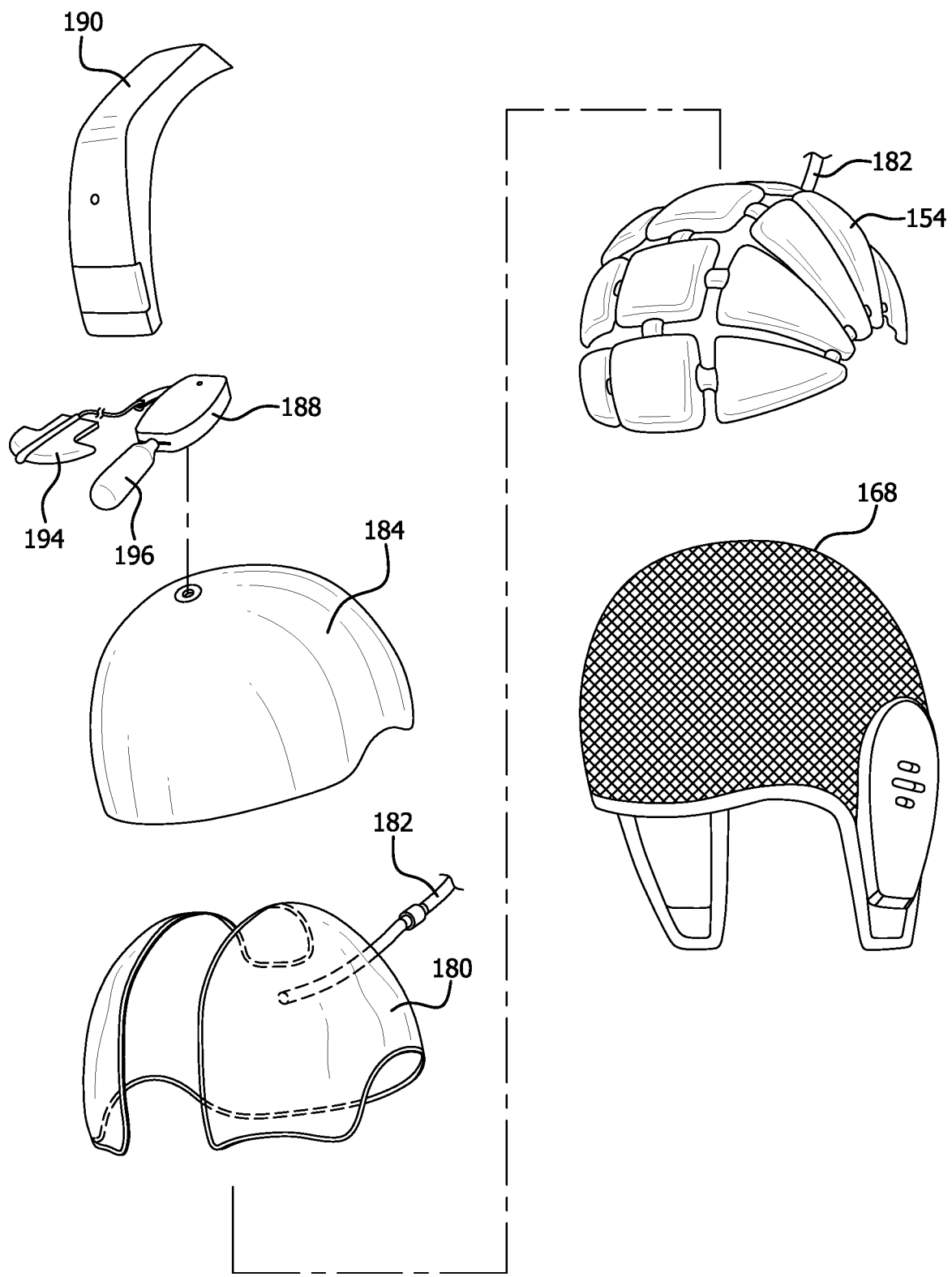
FIG. 20 is an exploded perspective view of the alternative embodiment.

An alternative embodiment of a headpiece 150 is shown in FIGS. 14-20. The headpiece includes a thermal reaction compartment layer 154, a liquid chamber 180, a gas chamber 184, and the gas canister assembly 188 with a cover 190 (FIG. 20). In this embodiment, the thermal reaction compartments 154 are standalone chambers or bladders that are interconnected by flow conduits 160 (FIGS. 16-17). The thermal reaction compartments 154 can be secured if desired to a supporting layer 164, or two and elastomeric layer 168 (FIG. 20). A water conduit 182 can connect the water chamber 180 to the reaction compartments 154. A pull tab 194 can operate to release gas from the gas canister 196.

Figure 21:
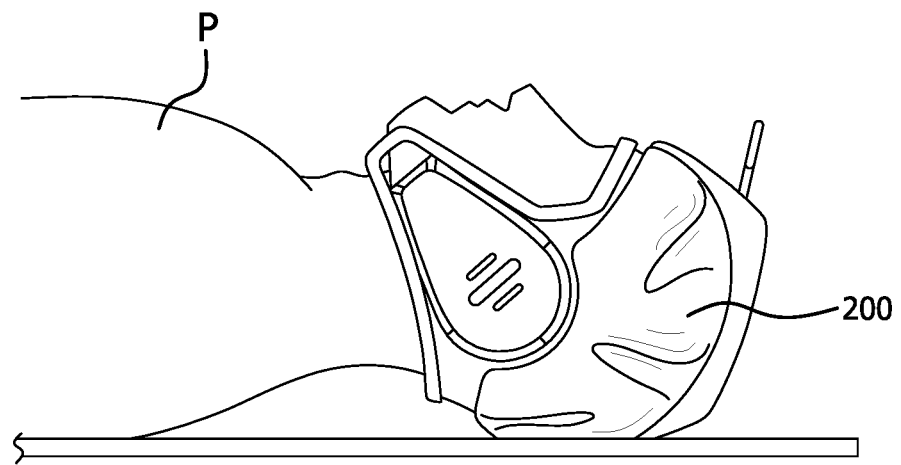
FIG. 21 is a schematic side elevation illustrating the apparatus of the invention on the head of a patient, in a first mode of operation.
Figure 22:
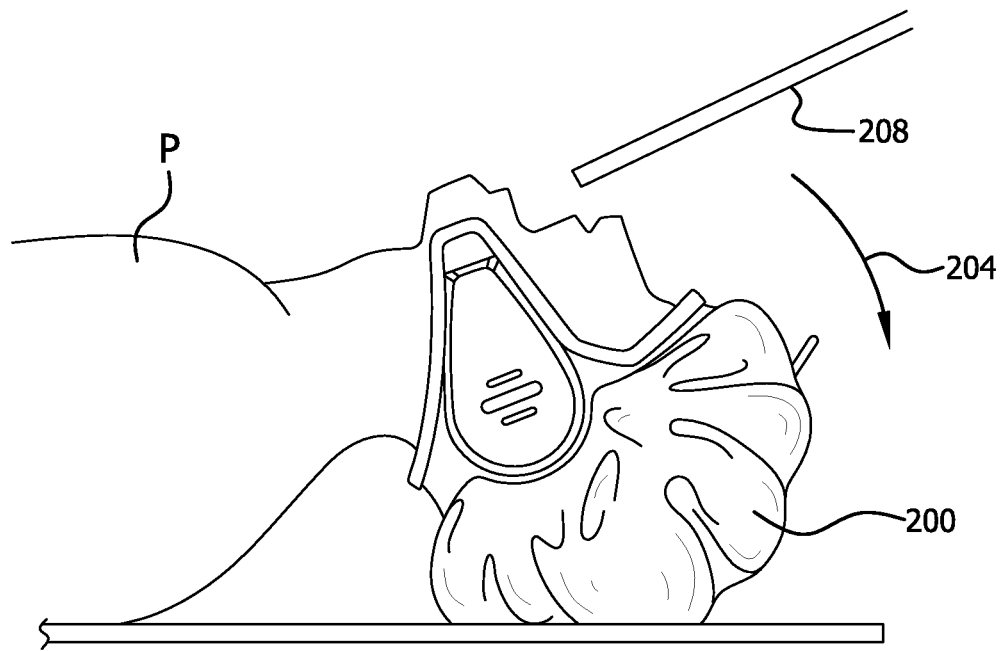
FIG. 22 is a schematic side elevation illustrating the apparatus of the invention head of the patient, in a second mode of operation.

The filling of the gas chamber of the invention simultaneously performs two functions. The filling of the gas chamber applies pressure on the liquid chamber to force liquid from the liquid chamber into the thermal reaction compartments. Also, the filling of the gas chamber creates a support and/or cushion for the corresponding body part of the patient P. This is shown in FIGS. 21-22. The cushioning can protect an injured portion of the patient. Inflation of the gas chamber can also be used to properly position the patient for emergency medical treatment. The headpiece 200 is inflated and as a result rotates the head of the patient P in the direction shown by the arrow 204. This positions the head and neck of the patient to receive an endotracheal intubation tube 208 to supply the patient with air. The gas chamber can be configured for other body parts or other purposes as desired.

Figure 23:
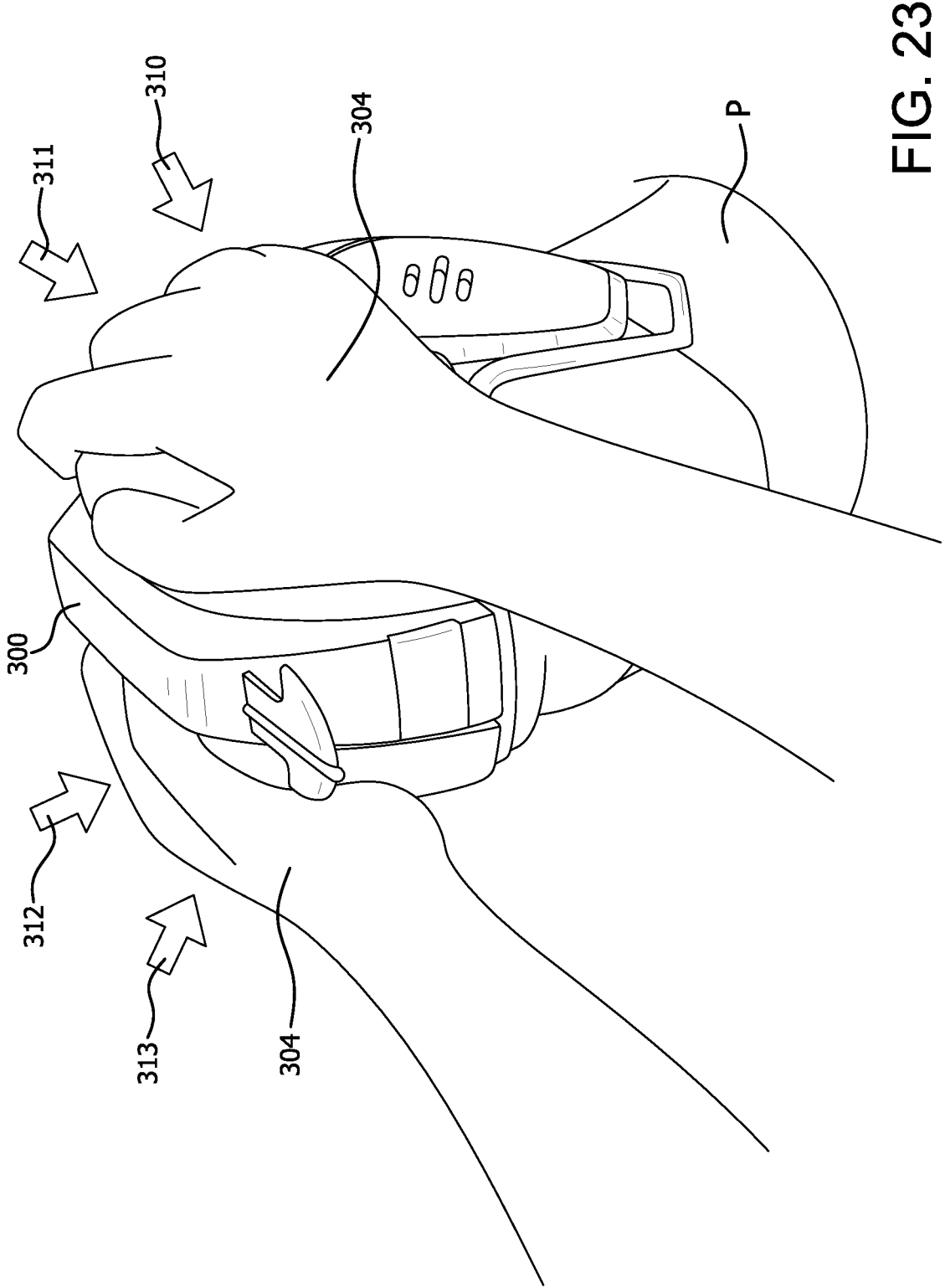
FIG. 23 is a schematic perspective view illustrating alternative manual operation of the thermal therapy apparatus.

There is shown in FIG. 23 and operation of the headpiece 300 for example where the gas canister for any reason is not operational. The hands 304 of the emergency medical practitioner can be used to physically force the liquid (water) from the liquid chamber as by squeezing in the direction of arrows 310-312. This will apply pressure to the liquid chamber and force liquid from the liquid chamber into the thermal reaction compartments.

Figure 24:
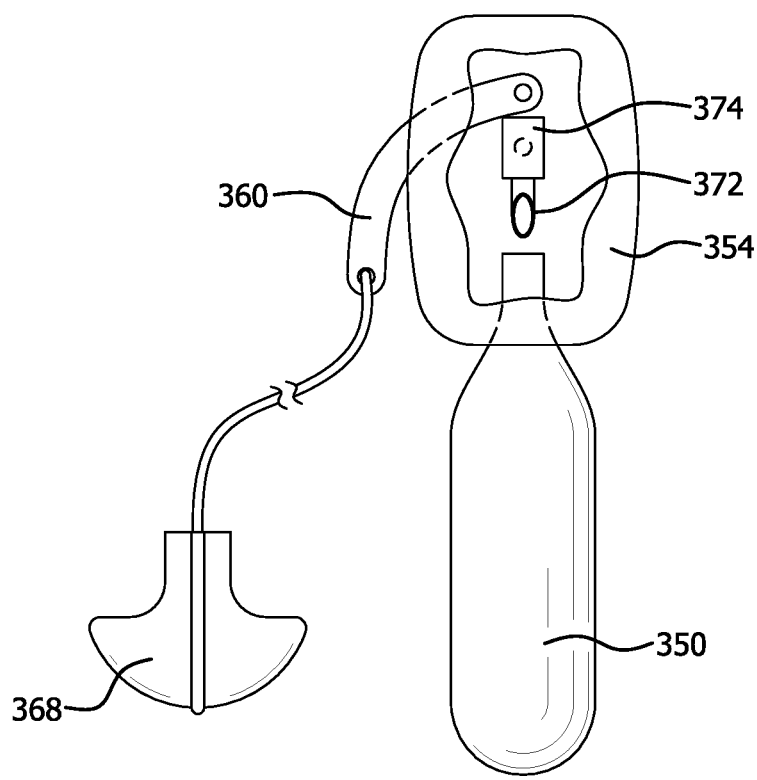
FIG. 24 is a plan view of a gas canister assembly, partially broken away.
Figure 25:
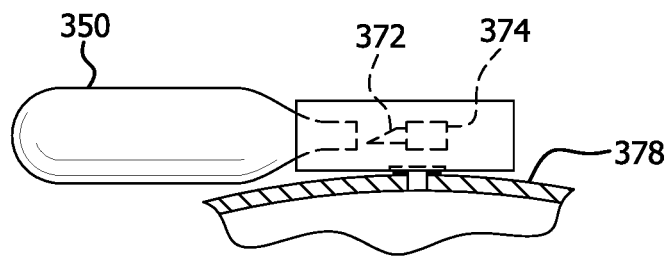
FIG. 25 is a cross-section of a gas canister assembly, partially in phantom.
Figure 26:
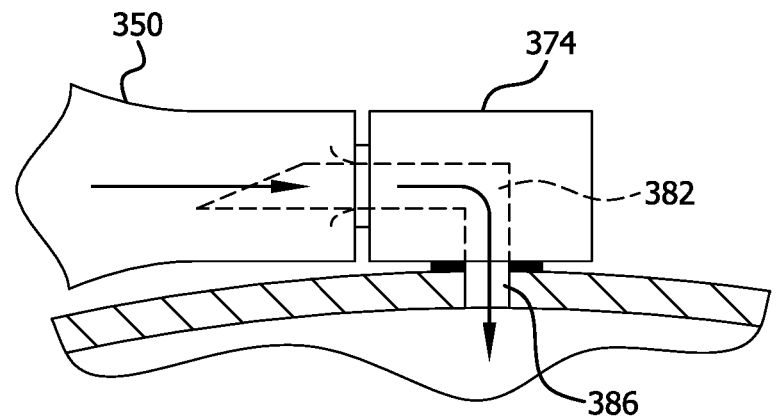
FIG. 26 is an enlarged schematic cross-section illustrating the operation of a gas canister assembly, partially in phantom.

The gas canister assembly can be of any suitable construction, and many different constructions are possible. There is shown in FIGS. 24-26 a gas canister assembly in which a pressurized gas canister 350 is secured to a body 354 which includes an actuating lever 360 connected to pull tab 368. The actuating lever 360 is also connected to a needle 372 through a needle housing 374. The body 354 is secured to the gas chamber 378. Upon the operation of the pull tab 368, needle 372 is driven through a hermetic seal of the pressurized gas canister 350 (FIG. 26). Needle 372 has an internal gas passage communicating with the gas passage 382 and the needle housing 374. An opening 386 is provided in the gas chamber 378 to permit the flow of pressurized gas from the gas canister 350 through the needle housing 374 and opening 386 into the gas chamber 378. Other gas canister constructions are possible.

Figure 27:
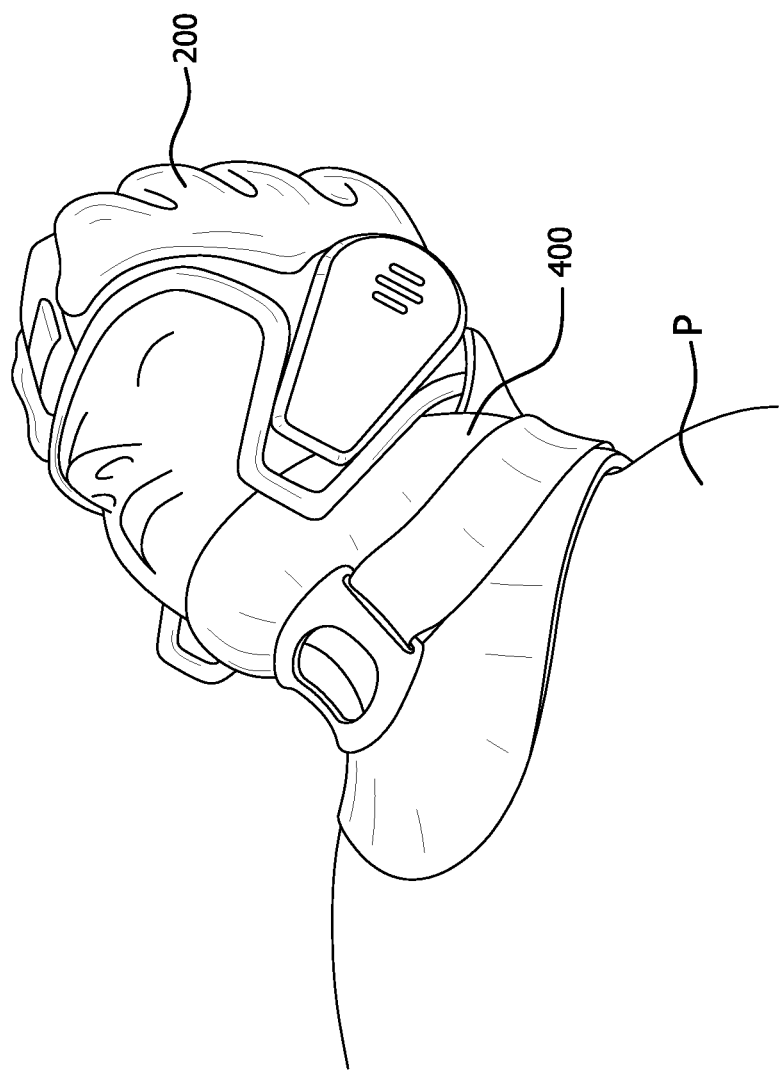
FIG. 27 is a perspective view of a patient with thermal therapy apparatus of the invention in use with a supportive neck brace.
Figure 28:
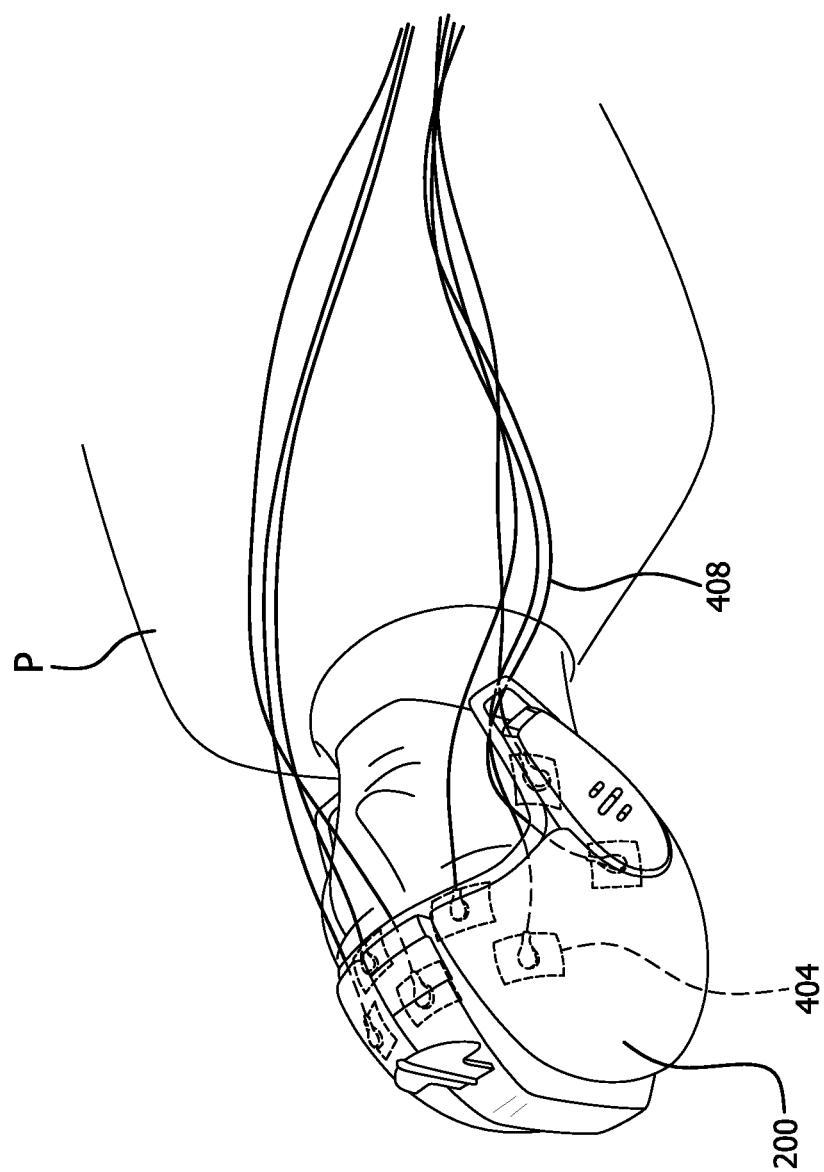
FIG. 28 is a perspective view of a patient with thermal therapy apparatus of the invention in use with patient monitoring equipment.

The invention can be used in conjunction with other standard emergency medical treatment equipment. There is shown in FIG. 27 a headpiece 200 according to the invention. A standard neck brace 400 is shown to fit on the patient P while the headpiece 200 is in use. In FIG. 28 there is shown the headpiece 200 used in connection with electroencephalogram (EEG) sensors 404 and connecting wires 408.

Figure 31:
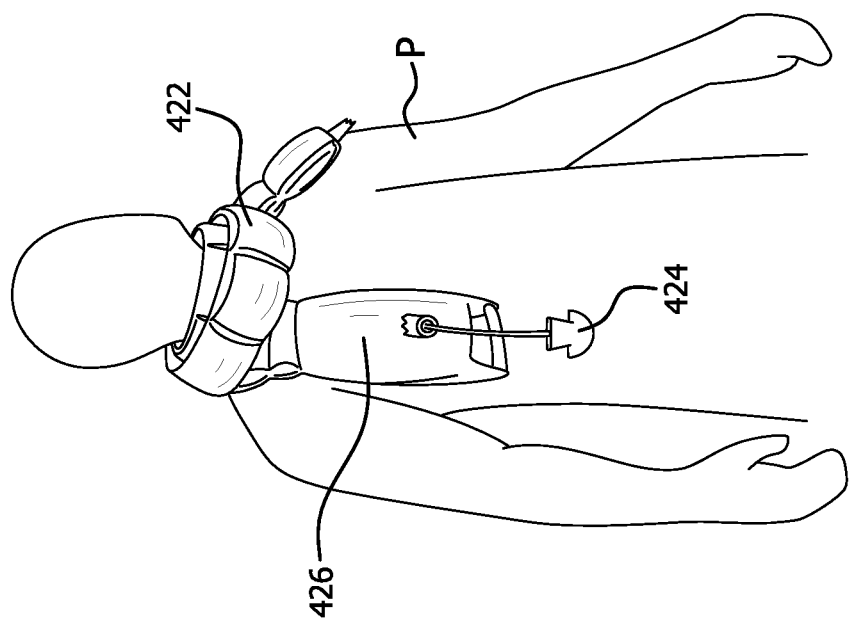
FIG. 31 is a perspective view of thermal therapy apparatus according to the alternative embodiment of FIGS. 29-30 in use on a patient.
Figure 29:
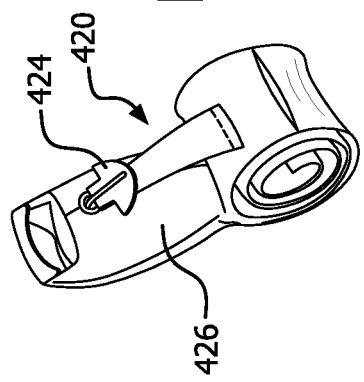
FIG. 29 is a perspective view of thermal therapy apparatus according to an alternative embodiment, in a first mode of operation.
Figure 30:
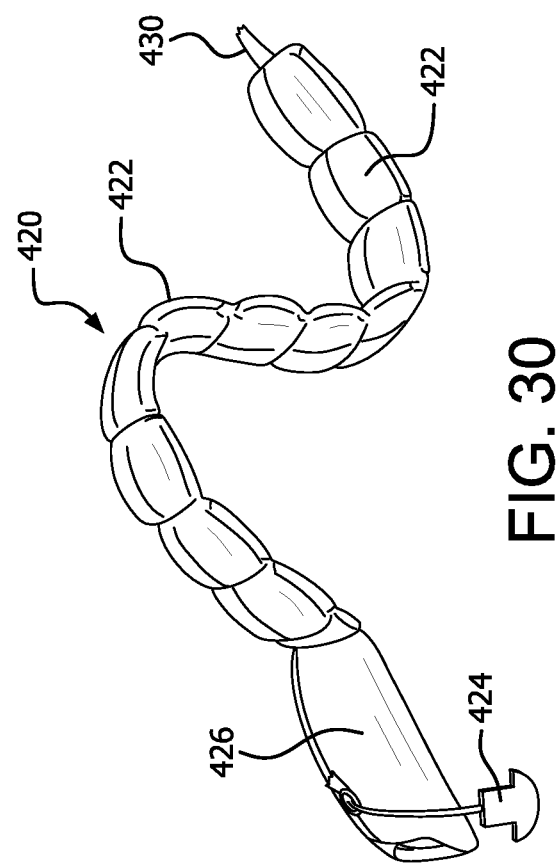
FIG. 30 is a perspective view of thermal therapy apparatus according to the alternative embodiment of FIG. 29, in a second mode of operation.

The invention is suitable for use in other emergency medical treatment procedures in addition to head trauma. One such device is shown in FIGS. 29-31. The device 420 is elongated and provides a series of thermal reaction compartments 422. A gas canister assembly can be secured within one or more compartments 426. A pull tab 424 can extend outward from the compartment 426. Upon operation of the pull tab 424, gas will be released from a pressurized gas container within compartment 426 and will force liquid from a liquid chamber (not shown) to reaction compartments 422 which can be linked by suitable liquid conduits. Securing structures 430 such as a buckle or hook and loop can be used to secure the device 420 in the desired position for example wrapped around the neck of the patient P (FIG. 31). Other constructions are possible.

The invention as shown in the drawings and described in detail herein disclose arrangements of elements of particular construction and configuration for illustrating preferred embodiments of structure and method of operation of the present invention. It is to be understood however, that elements of different construction and configuration and other arrangements thereof, other than those illustrated and described may be employed in accordance with the spirit of the invention, and such changes, alternations and modifications as would occur to those skilled in the art are considered to be within the scope of this invention as broadly defined in the appended claims. In addition, it is to be understood that the phraseology and terminology employed herein are for the purpose of description and should not be regarded as limiting.

We claim:
1. Thermal therapy apparatus for a patient, comprising:
a flexible base for conforming to the patient;
a plurality of thermal reaction compartments, each thermal reaction compartment containing a first of at least two thermal reaction components, the thermal reaction compartments being interconnected by fluid conduits, each thermal reaction compartment being in thermal contact with a heat transfer surface for contacting the surface portion of the patient which will transfer heat to the patient, the thermal reaction components having an initial state where the thermal reaction components are separated from contact with each other, and a treatment state in which the thermal reaction components are placed into contact, wherein a thermal reaction takes place and transfers heat with the cooling surface and the corresponding surface portion of the patient;
a liquid chamber comprising a flexible wall and containing a second of the at least two thermal reaction components, the second thermal reaction component being a liquid, the liquid chamber being connected to the fluid conduits by a valve, wherein in an initial state all of the second thermal reaction component is provided in the liquid chamber, and the fluid conduits and the thermal reaction compartments are devoid of the second thermal reaction component;
a gas chamber adjoining the liquid chamber and the flexible wall;

a gas container having therein a pressurized gas, and a fluid connection between the gas container and the gas chamber, and a gas valve for selectively releasing the pressurized gas from the gas container through the fluid connection into the gas chamber;

wherein upon operation of the gas valve, pressurized gas will flow into the gas chamber and the gas in the gas chamber will apply pressure to the flexible wall and thereby to the liquid chamber and force the second thermal reaction component through the valve and into the fluid conduits and thereby into the thermal reaction compartments, where the at least two thermal reaction components will react and transfer heat with the heat transfer surface, and the presence of the gas within the gas chamber will support and cushion the patient.

2. The thermal therapy apparatus of claim 1, wherein the thermal therapy apparatus comprises an elastomeric liner.

3. The thermal therapy apparatus of claim 2, wherein the thermal reaction compartments are enclosed chambers connected by fluid conduits and secured to the plastic liner.

4. The thermal therapy apparatus of claim 1, wherein at least one of the thermal reaction components comprises ammonium nitrate, and the thermal reaction components comprises at least one selected from the group consisting of barium hydroxide and water.

5. The thermal therapy apparatus of claim 1, further comprising a thermometer for providing an indication of the temperature of at least one of the cooling members.

6. The thermal therapy apparatus of claim 1, further comprising a timer, the timer being activated by at least one selected from the group consisting of operation of the activation device and a temperature sensor.

7. The thermal therapy apparatus of claim 1, wherein the thermal therapy apparatus comprises a headpiece, and the headpiece comprises earpieces for locating the headpiece on a users head.

8. The thermal therapy apparatus of claim 1, wherein the thermal therapy apparatus comprises a headpiece, and wherein the thermal reaction compartments are positioned on the headpiece such that when the headpiece is positioned on a head of the patients the thermal reaction compartments and the heat transfer surfaces will contact at least one pulse point of the patient.

9. The thermal therapy apparatus of claim 8, wherein the pulse points comprise at least one selected from the group consisting of a forehead, a base of the neck, and the temples.

10. The thermal therapy apparatus of claim 1, wherein the liquid chamber is an enclosed bag positioned between the thermal reaction compartments and the gas chamber, the liquid chamber comprising a fluid outlet communicating with the valve and the thermal reaction compartments.

11. The thermal therapy apparatus of claim 1, wherein the thermal reaction components participate in an endothermic reaction.

12. A method for administering thermal therapy to a surface portion of a patient, comprising the steps of:

providing a thermal therapy device for a patient, comprising:

a flexible piece for conforming to a portion of the patient for receiving the thermal therapy;

a plurality of thermal reaction compartments, each thermal reaction compartment containing a first of at least two thermal reaction components, the thermal reaction compartments being interconnected by fluid conduits, each thermal reaction compartment being in thermal contact with a heat transfer surface for contacting the surface portion of the patient, the thermal reaction components having an initial state where the thermal reaction components are separated from contact with each other, and a treatment state in which the thermal reaction components are placed into contact, wherein a thermal reaction takes place and cools the cooling surface and the corresponding portion of the patient;

a liquid chamber comprising a flexible wall and containing a second of at last two thermal reaction components, the second thermal reaction component being a liquid, the liquid chamber being connected to the fluid conduits by a check valve, wherein in an initial state all of the second thermal reaction component is provided in the liquid chamber, and the fluid conduits and the thermal reaction compartments are devoid of the second thermal reaction component;

a gas chamber adjoining the liquid chamber and the flexible wall;

a gas container having therein a pressurized gas, a fluid connection between the gas container and the gas chamber, and a gas valve for selectively releasing the pressurized gas from the gas container through the fluid connection into the gas chamber;

and, operating the gas valve to place the thermal reaction components into contact with each other, wherein upon operation of the gas valve, pressurized gas will flow into the gas chamber and the gas in the gas chamber will apply pressure to the flexible wall and thereby to the liquid chamber and force the second thermal reaction component through the check valve and into the fluid conduits and thereby into the thermal reaction compartments, where the at least two thermal reaction components will react and transfer heat between the thermal reaction compartments and the heat transfer surface, and the presence of the gas within the gas chamber will cushion the surface portion of the patient.

13. A method for administering thermal therapy to a surface portion of a patient, comprising the steps of:

providing a thermal therapy device for a patient, comprising:

a flexible piece for conforming to a portion of the patient for receiving the thermal therapy;

a plurality of thermal reaction compartments, each compartment containing a first of at least two thermal reaction components, the thermal reaction compartments being interconnected by fluid conduits, each thermal reaction compartment being in thermal contact with a heat transfer surface for contacting the surface portion of the patient which will transfer heat with the surface portion of the patient, the thermal reaction components having an initial state where the thermal reaction components are separated from contact with each other, and a treatment state in which the thermal reaction components are placed into contact, wherein a thermal reaction takes place and cools the cooling surface and the corresponding portion of the patient;

a liquid chamber comprising a flexible wall and containing a second of at least two thermal reaction components, the second thermal reaction component being a liquid, the liquid chamber connected to the fluid conduits by a check valve, wherein in an initial state all of the second thermal reaction component is provided in the liquid chamber and the fluid conduits and the thermal reaction compartments are devoid of the second thermal reaction component;

a gas chamber adjoining the liquid chamber;

a gas container having therein a pressurized gas, a fluid connection between the gas container and the gas chamber, and a gas valve for selectively releasing the pressurized gas from the gas container through the fluid connection into the gas chamber;
and,
operating the gas valve to place the thermal reaction components into contact with each other, wherein upon operation of the gas valve, pressurized gas will flow into the gas chamber and the gas in the gas chamber will apply pressure to the liquid chamber and force the thermal reaction component through the check valve and into the fluid conduits and thereby into the thermal reaction compartments, where the at least two thermal reaction components will react and transfer heat between the thermal reaction compartments and the heat transfer surface, and the presence of the gas within the gas chamber will cushion the surface portion of the patient.

\* \* \* \* \*

UNITED STATES PATENT AND TRADEMARK OFFICE
CERTIFICATE OF CORRECTION

| | | |
|---|---|---|
| PATENT NO. | : 11,278,447 B2 | Page 1 of 1 |
| APPLICATION NO. | : 16/582723 | |
| DATED | : March 22, 2022 | |
| INVENTOR(S) | : David Rand et al. | |

It is certified that error appears in the above-identified patent and that said Letters Patent is hereby corrected as shown below:

On the Title Page

The list of inventors should read as follows:
(72) Inventors: David Rand, Boca Raton, FL (US);
William Rand, Boca Raton, FL (US);
Felipe Echeverri, Pinecrest, FL (US);
Joseph Aguila, Fort Lauderdale, FL (US)

Signed and Sealed this
Ninth Day of January, 2024

Katherine Kelly Vidal
*Director of the United States Patent and Trademark Office*